(12) United States Patent
Young et al.

(10) Patent No.: US 7,534,429 B2
(45) Date of Patent: *May 19, 2009

(54) CYTOTOXICITY MEDIATION OF CELLS EVIDENCING SURFACE EXPRESSION OF CD63

(75) Inventors: David S. F. Young, Toronto (CA); Susan E. Hahn, Toronto (CA); Helen P. Findlay, Toronto (CA); Luis A. G. daCruz, Toronto (CA); Daad Sayegh, Mississauga (CA); Sheung Tat Fan, Hong Kong (CN); Ronnie Tung Ping Poon, Hong Kong (CN); Terence Kin Wah Lee, Hong Kong (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/493,407

(22) Filed: Jul. 26, 2006

(65) Prior Publication Data

US 2006/0269481 A1    Nov. 30, 2006

Related U.S. Application Data

(63) Continuation-in-part of application No. 11/321,624, filed on Dec. 29, 2005, now Pat. No. 7,431,923, which is a continuation-in-part of application No. 10/810,751, filed on Mar. 26, 2004, now Pat. No. 7,361,343, which is a continuation-in-part of application No. 10/603,006, filed on Jun. 23, 2003, which is a continuation-in-part of application No. 10/348,231, filed on Jan. 21, 2003, now Pat. No. 7,009,040, which is a continuation-in-part of application No. 09/727,361, filed on Nov. 29, 2000, now Pat. No. 6,657,048.

(51) Int. Cl.
A61K 31/395    (2006.01)

(52) U.S. Cl. .................................................. 424/130.1

(58) Field of Classification Search ............... 424/130.1
See application file for complete search history.

(56) References Cited

U.S. PATENT DOCUMENTS

| | | |
|---|---|---|
| 4,816,567 A | 3/1989 | Cabilly |
| 4,861,581 A | 8/1989 | Epstein et al. |
| 5,171,665 A | 12/1992 | Hellstrom et al. |
| 5,296,348 A | 3/1994 | Rakowicz-Szulczynska |
| 5,484,596 A | 1/1996 | Hanna, Jr. et al. |
| 5,693,763 A | 12/1997 | Codington et al. |
| 5,750,102 A | 5/1998 | Eisenbach et al. |
| 5,780,033 A | 7/1998 | Torchillin et al. |
| 5,783,186 A | 7/1998 | Arakawa et al. |
| 5,849,876 A | 12/1998 | Linsley et al. |
| 5,869,045 A | 2/1999 | Hellstrom et al. |
| 5,869,268 A | 2/1999 | Kudo et al. |
| 6,180,357 B1 | 1/2001 | Young et al. |
| 6,245,898 B1 | 6/2001 | Testa et al. |
| 6,657,048 B2 | 12/2003 | Young et al. |
| 6,783,961 B1 | 8/2004 | Edwards et al. |
| 6,783,969 B1 | 8/2004 | Tang et al. |
| 7,009,040 B2 | 3/2006 | Young et al. |
| 2002/0102638 A1 | 8/2002 | Rosen et al. |
| 2003/0055220 A1 | 3/2003 | Legrain |
| 2003/0148408 A1 | 8/2003 | Frantz et al. |
| 2003/0211498 A1 | 11/2003 | Morin et al. |
| 2004/0105816 A1 | 6/2004 | Young et al. |
| 2004/0141913 A1 | 7/2004 | Young et al. |
| 2004/0141915 A1 | 7/2004 | Young et al. |
| 2004/0197328 A1 | 10/2004 | Young et al. |
| 2004/0198651 A1 | 10/2004 | Klammer et al. |
| 2004/0258693 A1 | 12/2004 | Young et al. |
| 2006/0204497 A1 | 9/2006 | Young et al. |
| 2006/0210474 A1 | 9/2006 | Young et al. |

FOREIGN PATENT DOCUMENTS

| | | |
|---|---|---|
| AU | 0153140 A5 | 10/2001 |
| CN | 1326951 | 12/2001 |
| CN | 1326962 | 12/2001 |
| CN | 1351054 | 5/2002 |
| CN | 1364803 | 8/2002 |
| EP | 001461 | 4/1979 |

(Continued)

OTHER PUBLICATIONS

Jain (Scientific American, 271(1):58-65, Jul. 1994).*

(Continued)

*Primary Examiner*—Sean E Aeder
(74) *Attorney, Agent, or Firm*—McHale & Slavin, P.A.

(57) ABSTRACT

This invention relates to the diagnosis and treatment of cancerous diseases, particularly to the mediation of cytotoxicity of primary and metastatic human tumor cells; and most particularly to the use of an isolated monoclonal antibody or cancerous disease modifying antibodies (CDMAB) thereof, optionally in combination with one or more chemotherapeutic agents, as a means for initiating the cytotoxic response in such human tumors, e.g. any primary or metastatic tumor sites which arise from hepatocytes. The invention further relates to binding assays which utilize the CDMAB of the instant invention.

16 Claims, 12 Drawing Sheets
(9 of 12 Drawing Sheet(s) Filed in Color)

FOREIGN PATENT DOCUMENTS

| | | |
|---|---|---|
| EP | 00200610 | 11/1986 |
| EP | 266032 | 8/1987 |
| EP | 404097 | 6/1990 |
| EP | 404097 | 12/1990 |
| EP | 1033401 | 6/2000 |
| EP | 1033401 | 9/2000 |
| GB | 00003480 | 4/2000 |
| WO | WO9311161 | 6/1993 |
| WO | WO9966027 | 12/1999 |
| WO | WO0005918 | 2/2000 |
| WO | WO0034317 | 6/2000 |
| WO | WO0041798 | 7/2000 |
| WO | WO0055180 | 9/2000 |
| WO | WO0055280 | 9/2000 |
| WO | WO0175177 | 10/2001 |
| WO | WO0175177 A2 | 10/2001 |
| WO | WO01751772 | 10/2001 |
| WO | WO0200677 | 1/2002 |
| WO | WO02055551 | 7/2002 |
| WO | WO02057303 | 7/2002 |
| WO | WO02070539 | 9/2002 |
| WO | WO03016475 | 2/2003 |
| WO | WO03057160 | 7/2003 |
| WO | WO03006828 | 8/2003 |
| WO | WO03068268 | 8/2003 |
| WO | WO03070902 | 8/2003 |
| WO | WO03086456 | 10/2003 |
| WO | WO/03088808 | 10/2003 |
| WO | WO2004041170 | 5/2004 |

OTHER PUBLICATIONS

Chatterjee (Cancer Immunol. Imunother., 38:75-82, 1994).*
Weiner L. M. (Seminars in Oncology, 26 (4 Suppl 12):41-50, Aug. 1999).*
Seaver (1994; Genetic Engineering News, 14(14): pp. 10 and 21).*
Tockman et al (Cancer Res., 1992, 52:2771 1s-2718s).*
Jain et al (Scientific American, 271(1):58-65, Jul. 1994).*
Chatterjee et al (Cancer Immunol. Imunother., 38:75-82, 1994, see Introduction).*
M. Adachi et al, "Novel staging protocol for non-small-cell lung cancers according to MRP-1/CD9 and KAII/CD82 gene expression", J. Clin. Oncol., 16(4):1397-1406 (Apr. 1998).
G. Andreola et al, "Induction of lymphocyte apoptosis by tumor cell secretion of FasL-bearing microvesicles", J. Exp. Med., 195(10)1303-1316 (May 2002).
B. Atkinson et al, "Monoclonal antibody to a highly glycosylated protein reacts in fixed tissue with melanoma and other tumors", Hybridoma, 4(3):243-255 (1985).
D. Azorsa et al, "A general approach to the generation of monoclonal antibodies against members of the tetraspanin superfamily using recombinant GST fusion proteins", J. Immunol. Meth., 229:35-48 (1999).
M. Barrio et al, "A new epitope on human melanoma-associated antigen CD63/ME491 expressed by both primary and metastatic melanoma", Hybridoma, 17(4):355-364 (1998).
M. Barrio et al, "Monoclonal antibody FC-5.01, directed against CD63 antigen, is internalized into cytoplasmic vesicles in the IIB-BR-G human breast cancer cell line", Hybridoma, 17(6):517-523 (1998).
F. Berditchevski et al, "Characterization of integrin-tetraspanin adhesion complexes: role of tetraspanins in integrin signaling", J. Cell Biol., 146(2):477-492 (Jul. 1999).
F. Berditchevski et al, "A novel link between integrins, transmembrane-4 superfamily proteins (CD63 and CD81) and phosphatidylinositol 4-kinase", J. Biol. Chem., 272(5):2595-2598 (Jan. 1997).
F. Berditchevski et al, "Specific association of CD63 with the VLA-3 and VLA-6 integrins", J. Biol. Chem., 270 (30):17784-17790 (Jul. 1995).

D. Blakey et al, "Antitumor activity of the novel vascular targeting agent ZD6126 in a panel of tumor models", Clinical Cancer Research, 8:1974-1983 (Jun. 2002).
A. Carmo et al, "Association of the transmembrane 4 superfamily molecule CD53 with a tyrosine phosphatase activity", Eur. J. Immunol., 25:2090-2095 (1995).
C. Claas et al, "Evaluation of prototype transmembrane 4 superfamily protein complexes and their relation to lipid rafts", J. Biol. Chem., 276(11):7974-7984 (Mar. 2001).
D. Demetrick et al, "ME491 melanoma-associated glycoprotein family: antigenic identity of ME491, NKI/C-3, neuroglandular antigen (NGA), and CD63 proteins", J. Natl. Cancer Inst., 84(6):422-429 (Mar. 1992).
G. Eckhardt et al, "Developmental therapeutics: successes and failures of clinical trial designs of targeted compounds", in American Society of Clinical Oncology, pp. 209-219 (2003).
A. Engering et al, "Association of distinct tetraspanins with MHC class II molecules at different subcellular locations in human immature dendritic cells", International Immunology, 13(2):127-134 (2001).
J-M. Escola et al, "Selective enrichment of tetraspan proteins on the internal vesicles of multivesicular endosomes and on exosomes secreted by human B-lymphocytes", J. Biol. Chem., 273(32):20121-20127 (Aug. 1998).
S. Guichard et al, "Schedule-dependent activity of topotecan in OVCAR-3 ovarian carcinoma xenograft pharmacokinetic and pharmacodynamic evaluation", Clinical Cancer Research, 7:3222-3228 (Oct. 2001).
N. Guilbaud et al, "Marked antitumor activity of a new potent acronycine derivative in orthotopic models of human solid tumors", Clinical Cancer Research, 7:2573-2580 (Aug. 2001).
C. Hammond et al, "the tetraspan protein CD82 is a resident of MHC class II compartments where it associates with HLA-DR, -DM, and -DO molecules", J. Immunol., 161:3282-3291 (1998).
J. Hildreth et al, "Characterization of a novel self-associating Mr 40,000 platelet glycoprotein", Blood, 77(1):121-132 (Jan. 1991).
S. Hirschfeld et al, "Oncology drug development: United States Food and Drug Administration perspective", Critical Reviews in Oncology/Hematology, 42:137-143 (2002).
H. Hotta et al, "Genomic structure of the ME491/CD63 antigen gene and functional analysis of the $5^1$-flanking regulatory sequences", Biochem Biophys Res Comm, 185(1):436-442 (May 1992).
H. Hotta e tal, "Molecular cloning and characterization of an antigen associated with early stages of melanoma tumor progression", Cancer Research, 48:2955-2962 (Jun. 1988).
H. Hotta et al, "Overexpression of the human melanoma-associated antigen ME491 patially suppresses in vivo malignant phenotypes of H-ras-transformed NIH3T3 cells in athymic nude mice", Melanoma Research, 1:125-132 (1991).
C. Huang et al, "Correlation of reduction in MRP-1/CD9 and KAI1/CD82 expression with recurrences in breast cancer patients", Am J Pathol, 153(3):973-983 (Sep. 1998).
H-I. Jang et al, "A decrease in the expression of CD63 tetraspanin protein elevates invasive potential of human melanoma cells", Experimental and Molecular Medicine, 35(4):317-323 (Aug. 2003).
C. Joyner et al, "Identification and enrichment of human osteoprogenitor cells by using differentiation stage-specific monoclonal antibodies", Bone, 21(1):1-6 (Jul. 1997).
T. Karpanen et al, "Vascular endothelial growth factor C promotes tumor lymphangiogenesis and intralymphatic tumor growth", Cancer Research, 61:1786-1790 (Mar. 2001).
S. Kennel et al, "Monoclonal antibody to rat CD63 detects different molecular forms in rat tissue", Hybridoma, 17 (6):509-515 (1998).
G. Klement et al, "Differences in therapeutic indexes of combination metronimic chemotherapy and anti-VEGFR-2 antibody in multidrug-resistant human breast cancer xenografts", Clinical Cancer Research, 8:221-232 (Jan. 2002).
T. Kobayashi et al, "the tetraspanin CD63/lamp3 cycles between endocytic and secretory coompartments in human endothelial cells", Molecular Biology of the Cell, 11:1829-1843 (May 2000).

M. Kondoh et al, "Decreased expression of human melanoma-associated antigen ME491 along the progression of melanoma precanceroses to invasive and metastatic melanomas", Melanoma Research, 3:241-245 (1993).

Y. Koyama et al, "A novel monoclonal antibody induces the differentiation of monocyte leukemic cells", Biochem Biophys Res Comm, 168(3):898-904 (May 1990).

Y. Koyama et al, "CD63, a member of tetraspan transmembrane protein family, induces cellular spreading by reaction with monoclonal antibody on substrata", Biochem Biophys Res Comm, 246(3):841-846 (1998).

S. Lebel-Binay et al, "CD82, member of the tetra-span-transmembrane protein family, is a costimulatory protein fo rT cell activation", J. Immunol., 155:101-110 (1995).

J. Li et al, "Recombinant CD63/ME491/neuroglandular/NKI/C-3 antigen inhibits growth of established tumors in transgenic mice", J. Immunol., 171:2922-2929 (2003).

B. Mannion et al, "Transmembrane-4 superfamily proteins CD81 (TAPA-1), CD82, CD63, and CD53 specifically associate with integrin alpha4beta1 (CD49d/CD29)", J. Immunol., 157:2039-2047 (1996).

T. Martin, "Phosphoinositide lipids as signaling molecules: common themes for signal transduction, cytoskeletal regulation, and membrane trafficking", Annu. Rev. Cell Dev. Biol., 14:231-264 (1998).

M. Martinez-Lorenzo et al, "Unusual intracellular trafficking of salmonella typhimurium in human melanoma cells", Cellular Microbiology, 3(6):407-416 (2001).

M. Metzelaar et al, "CD63 antigen", J. Biol. Chem., 266(5):3239-3245 (Feb. 1991).

H. Nieuwenhuis et al, "Studies with a monoclonal antibody against activated platelets: evidence that a secreted 53,000-molecular weight lysosome-like granule protein is exposed on the surface of activated platelets in the circulation", Blood, 70(3):838-845 (Sep. 1987).

H. Okochi et al, "Expression of tetra-spans transmembrane family (CD9, CD37, CD53, CD63, CD81 and CD82) in normal and neoplastic human keratinocytes an association of CD9 with alpha3beta1 integrin", British Journal of Dermatology, 137:856-863 (1997).

K. Olson et al, "Inhibition of prostate carcinoma establishment and metastatic growth in mice by an antiangiogenin monoclonal antibody", Int. J. Cancer, 98:923-929 (2002).

P. Peters et al, "Cytotoxic T lymphocyte granules are secretory lysosomes, containing both perforin and granzymes", J. Exp. Med., 173:1099-1109 (May 1991).

K. Radford et al, "CD63 associates with transmembrane 4 superfamily members, CD9 and CD81, and with beta1 integrins in human melanoma", Biochem Biophys Res Comm, 222:13-18 (1996).

K. Radford et al, "Regulation of tumor cell motility and migration by CD63 in a human melanoma cell line", J. Immunol., 158:3353-3358 (1997).

K. Radford et al, "Suppression of human melanoma cell growth and metastasis by the melanoma-associated antigen CD63 (ME491)", Int. J. Cancer, 62:631-635 (1995).

E. Rubinstein et al, "CD9, CD63, CD81, and CD82 are components of a surface tetraspan network connected to HLA-DR and VLA integrins", Eur. J. Immunol., 26:2657-2665 (1996).

G. Sauer et al, "Expression of tetraspanin adaptor proteins below defined threshold values is associated with in vitro invasiveness of mamary carcinoma cells", Oncology Reports, 10:405-410 (2003).

Si and Hersey, "Expression of the neuroglandular antigen and analogues in melanoma, CD9 expression appears inversely related to metastatic potential of melanoma", Int. J. Cancer, 54:37-43 (1993).

L. Sikora et al, "Characterization of a novel neuroglandular antigen (NGA) expressed on abnormal human melanocytes", Int. J. Cancer, 39:138-145 (1987).

P. Sincock et al, "Localization of the transmembrane 4 superfamily (TM4SF) member PETA-3 (CD151) in normal human tissues: comparison with CD9, CD63, and alpha5beta1 integrin", J. Histochem Cytochem, 45:515-525 (1997).

K. Skubitz et al, "CD63 associates with CD11/CD18 in large detergent-resistant complexes after translocation to the cell surface in human neutrophils", FEBS Letters, 469:52-56 (2000).

K. Skubitz et al, "CD63 associates with tyrosine kinase activity and CD11/CD18, and transmits an activation signal in neutrophils", J. Immunol., 157:3617-3626 (1996).

P. Smith et al, "Anti-interleukin-6 monoclonal antibody induces regression of human prostate cancer xenografts in nide mice", The Prostate, 48:47-53 (2001).

R. Stephen et al, "A novel oestrogen-regulated gene in human breast cancer cells identified by differential display", J. Mel. Endocrin., 20:375-380 (1998).

V. Toothill et al, "Characterization of the enhanced adhesion of neutrophil leukocytesa to thrombin-stimulated endothelial cells", J. Immunol., 145(1):283-291 (Jul. 1990).

P. Therasse et al, "New guidelines to evaluate the response to treatment in solid tumors", Journal of the National Cancer Institute, 92(3):205-216 (Feb. 2000).

B. Ulbricht et al, "Influence of 12(S)-hydroxyeicosatetraenoic acid (12(S)-HETE) on the localization of cathepsin B and cathepsin L in human lung tumor cells", Eur. J. Cell. Biol., 74:294-301 (Nov. 1997).

C. Vennegoor et al, "Circulating melanoma-associated natigen detected by monoclonal antibody NKI/C-3", Cancer Immunol Immunother., 23:93-100 (1986).

V. Von Gruenigen et al, "Efficacy of intraperitoneal adenovirus-mediated p53 gene therapy in ovarian cancer", Int. J. Gynecol. Cancer, 9:365-372 (1999).

M. Wang et al, "An ocular melanoma-associated antigen", Arch Ophthalmol., 110:399-404 (1992).

W. Waud et al, "Characterization of in vivo mammary and prostate tumor xenograft models for growth and response to clinical anticancer agents", Contrib Oncol Basel Karger, 54:305-315 (1999).

Z. Xiao et al, "Generation of a baculovirus recombinant prostate-specific membrane antigen and its use in the development of a novel protein biochip quantitative immunoassay", Protein Expression and Purification, 19:12-21 (2000).

R. Yauch et al, "Specific interactions among transmembrane 4 superfamily (TM4SF) proteins and phosphoinositide 4-kinase", Biochem J., 351-629-637 (2000).

A. Zannettino et al, "A powerful new technique for isolating genes encoding cell surface antigens using retroviral expression cloning", J. Immunol., 156:611-620 (1996).

A. Zannettino et al, "Molecular cloning of the cell surface antigen identified by the osteoprogenitor-specific monoclonal antibody, HOP-26", J. Cell. Biochem., 89:56-66 (2003).

Oren et al, "TAPA-1, the target of an antiproliferative antibody, defines a new family of transmembrane proteins", Molecular and cellular biology, 10(8):4007-4015 (Aug. 1990).

G. Kohler et al, "Continuous cultures of fused cells secreting antibody of predefined specificity", Nature, 256:495-497 (Aug. 1975).

D. Paus et al, "Mapping epitopes and antigenicity by site-directed masking", Proc Natl Acad Sci, 103(24):9172-9177 (Jun. 2006).

Vennegoor et al, "Int. J Cancer", Cancer Immunol Immunother., 35(23):287-95 (1985).

Demetrick, et al. J. Nat'l Cancer Inst., ME491 Melanoma-Associated Glycoprotein Family: Antigenic Identity of ME491, NKI/C-3, Neuroglandular antigen (NGA), and CD63 Proteins, 84(6):422-9 (1992).

Gruters, et al, Cancer Res. 49(2):459-65 (1989).

Atkinson, et al., "Hybridoma", Monoclonal Antibody to a Highly Glycosylated Protein Reacts in Fixed Tissue With melanoma and Other Tumors, 4,243-255 (1984).

Folberg, et al., "Arch Ophthalmol" An Antimelanoma Monoclonal Antibody and the Histopathology of Uveal melanomas, 103(2):275-9 (1985).

Damato, et al., "Invest Ophthalmol Vis Sci." 27(9):1362-7 (1986).

Mantezazza, et al., "Blood", CD63 Tetraspanin Slows Down Cell Migration and Translocates to the Endosomal-Lysosomal-MIICs Route After Extracellular Stimuli in Human Immature Dendritic Cells, 104(4):1183-90 (2004).

Xu, et al., "Embo J", 23(4):811-22 (2004).

Can Res, 49:2955, Jun. 1, 1998.

Clackson, et al., Making Antibody Fragments Using Phase Display Libraries,Nature, 1991, 352:624-628.

Marks, et al., 1991, J. Mol. Biol., 222:581-597.

Ravetch and Kinet, Structure of the Human Immunoglobulin Locus: Characterization of Embryonic and Rearranged J and D Genes, Annu. Rev. Innunol, 9:457-92 (1991).

Clynes, et al., Fc Receptors Are Required in Passive and Active Immunity to Melanoma, PNAS (USA), 1998, 95:652-656.

Daeron, Review M, Annu. Rev. Immunol, 15:203-234 (1997).

Capel, et al., Heterogeneity of Human IgG Fc Receptors, Immunomethods 4:25-34 (1994).

deHaas, et al., J. Lab. Clin. Med., 126:330-41 (1995).

Guyer, et al., Binding By Mouse Intestinal Epithelial Cell Receptors, J. Immunol, 117:587 (1976).

Kim, et al., Localization of the Site of the Murine IgG1 Molecule That Is Involved in Biding to the Murine Intestinal Fc Receptor, Eur. J. Immunol, 24:2429 (1994).

Gazzano-Santoro, et al., A Non-Radioactive Complement-Dependent Cytotoxicity Assay For Anti-CD20 Monoclonal Antibody, J. Immunol, Methods 202:163 (1996).

Kabat, et al., Sequences of Proteins of Immunological Interest, 1991, 5th Ed., Public Health Service, National Institutes of Health, Bethesda, MD.

Chothia and Lesk, Canonical Structures for the Hypervariable Regions of Immunoglobulins, J. Mol. Biol. 1987, 196:901-917.

Pluckthun, "The Pharmacology of Monoclonal Antibodies", vol. 113, 1994, Rosenburg and Moore Eds., Springer-Verlag, New York, pp. 269-315.

Hollinger, et al., Proc. Natl. Acad. Sci., USA, 1993, 90:6444-6448.

Froehler, et al., Nucl. Acids Res., 1986, 14:5399-5407.

Morrison, et al., Proc. Natl. Acad. Sci., USA, 1984, 81:6851-6855.

L. Belanger, C. Sylvestre, and D. Dufour, Enzyme Linked Immunoassay for Alpha Fetoprotein by Competitive and Sandwich Procedures, 1973, Clinica Chimica Acta 48, 15.

* cited by examiner

FIGURE 1

| Summary diagnosis Liver Cancer | | | | | | | | |
|---|---|---|---|---|---|---|---|---|
| 7BD-33-11A | | | | | | | | |
| Diagnosis | | Total | - | +/- | + | ++ | +++ | Total Positive | % of Positive |
| Tumor | | 49 | 10 | 3 | 18 | 15 | 3 | 39 | 80% |
| Primary HCC | | 37 | 8 | 3 | 14 | 9 | 3 | 29 | 78% |
| Metastatic HCC | | 8 | 1 | 0 | 2 | 5 | 0 | 7 | 88% |
| Primary Cholangiocarcinoma | | 2 | 1 | 0 | 1 | 0 | 0 | 1 | 50% |
| Metastatic Cholangiocarcinoma | | 2 | 0 | 0 | 1 | 1 | 0 | 2 | 100% |
| | Histological grade | | | | | | | | |
| Primary HCC | Well Diffrentiated | 5 | 1 | 0 | 0 | 4 | 0 | 4 | 80% |
| | Moderatly Diffrentiated | 19 | 3 | 1 | 9 | 3 | 3 | 16 | 84% |
| | Poorly Diffrentiated | 4 | 0 | 1 | 2 | 1 | 0 | 4 | 100% |
| | Unknown | 9 | 4 | 1 | 3 | 1 | 0 | 5 | 56% |
| Tumor Stages (AJCC) | I | 2 | 1 | 0 | 0 | 1 | 0 | 1 | 50% |
| | II | 17 | 2 | 2 | 7 | 5 | 1 | 15 | 88% |
| | III | 16 | 4 | 1 | 7 | 3 | 1 | 12 | 75% |
| | IV | 8 | 3 | 0 | 2 | 2 | 1 | 5 | 63% |
| Normal | | 9 | 0 | 0 | 1 | 3 | 5 | 9 | 100% |

FIGURE 2
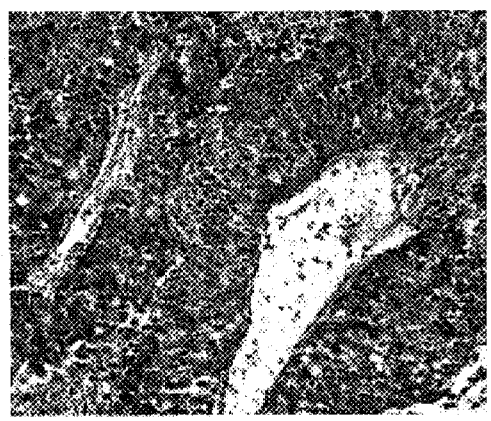
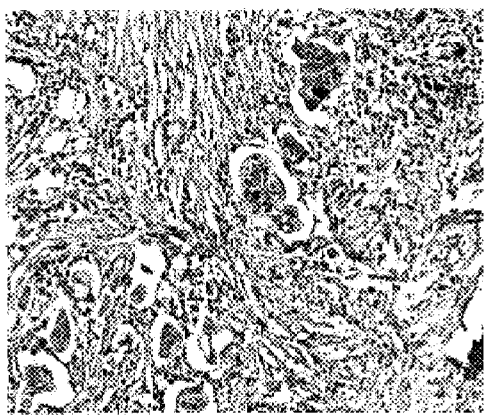
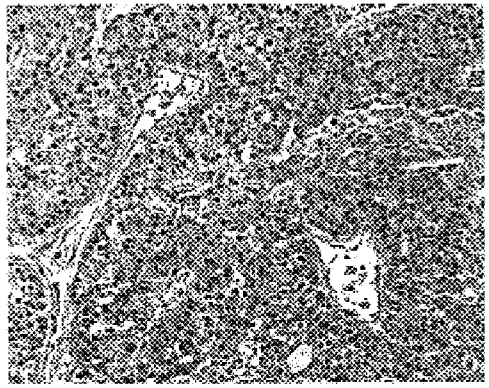
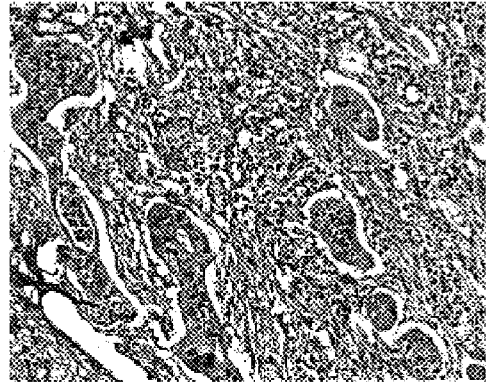

FIGURE 3
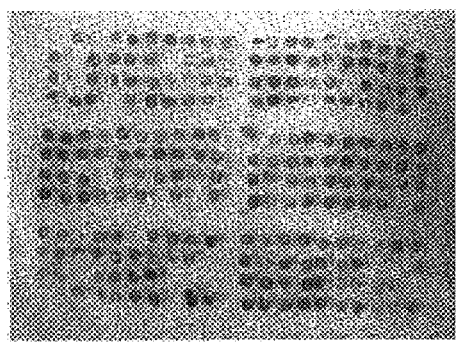
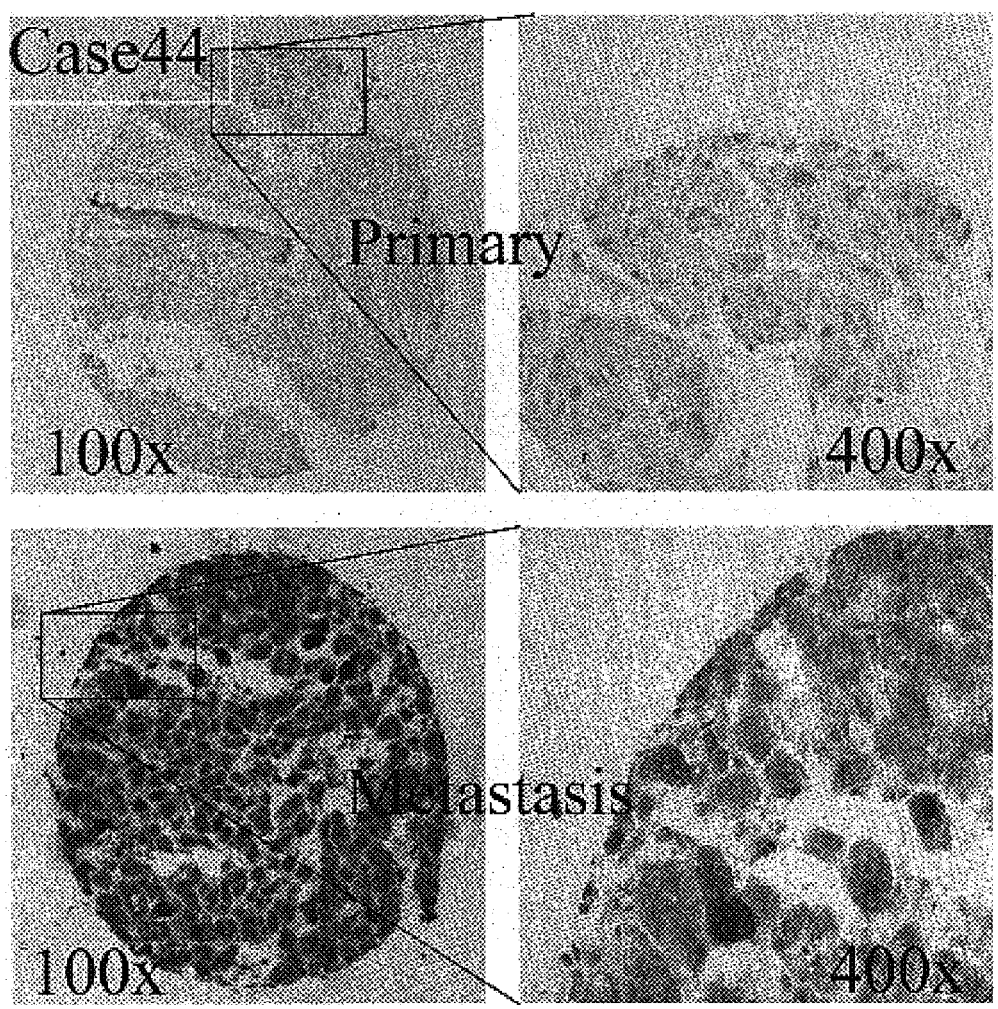

FIGURE 4

| P<0.01 | CD63 expression | | |
|---|---|---|---|
| | Negative (-ve) | Weak (+) | Moderate-strong (+++) |
| Primary HCC | 10/54(19%) | 18/54 (33%) | 26/54(48%) |
| Metastatic HCC | 2/57 (4%) | 12/57 (21%) | 43/57 (75%) |

FIGURE 6

| Linicopathological variables | Number | CD63 expression | | p |
| --- | --- | --- | --- | --- |
| | | weak to low expression | moderate to high expression | |
| Sex | | | | |
| Male | 42 | 7 | 35 | 0.059 |
| Female | 8 | 4 | 4 | |
| Age | | | | |
| ≤median, 52.5 | 25 | 4 | 21 | 0.496 |
| >median, 52.5 | 25 | 7 | 18 | |
| Serum AFP level | | | | |
| Low (≤20 ng/mL) | 21 | 3 | 18 | 0.482 |
| High (>20 ng/mL) | 28 | 7 | 21 | |
| Encapsulation | | | | |
| Yes | 12 | 3 | 9 | 0.378 |
| No | 31 | 4 | 27 | |
| Venous infilration | | | | |
| Absent | 25 | 12 | 1 | 0.001* |
| Present | 25 | 13 | 24 | |
| TNMNew | | | | |
| Early stage (I-II) | 23 | 9 | 14 | 0.014* |
| Late stage (III-IV) | 27 | 2 | 25 | |
| Recurrence in the first year | | | | |
| Yes | 28 | 1 | 27 | 0.001* |
| No | 22 | 10 | 12 | |
| Tumor size | | | | |
| Small (≤5cm) | 14 | 6 | 8 | 0.055 |
| Large (>5cm) | 29 | 4 | 25 | |
| HBV association | | | | |
| Positive for HBsAg | 45 | 10 | 35 | 1.000 |
| Negative for HBsAg | 5 | 1 | 4 | |

FIGURE 8
A
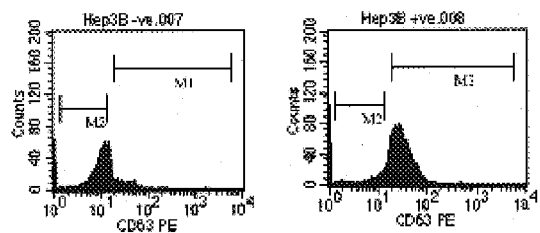
B
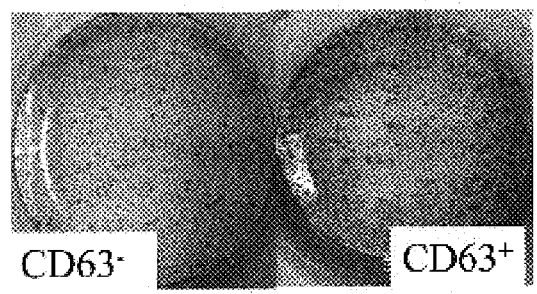 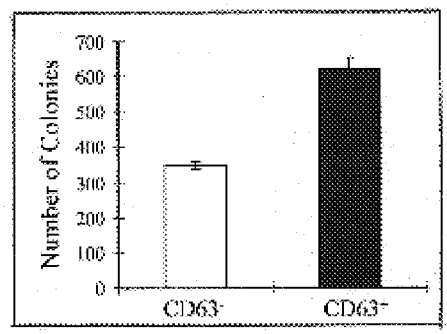
C
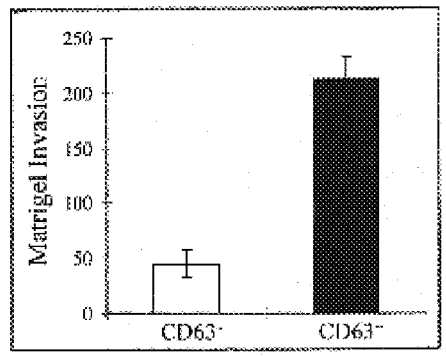
D
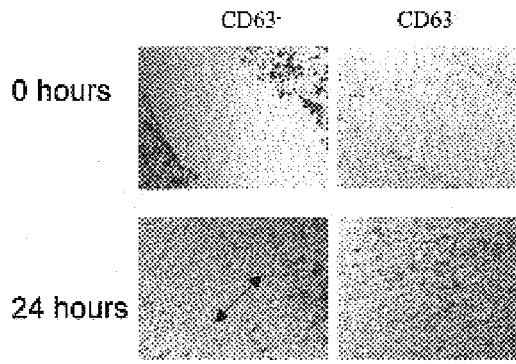

FIGURE 9
A
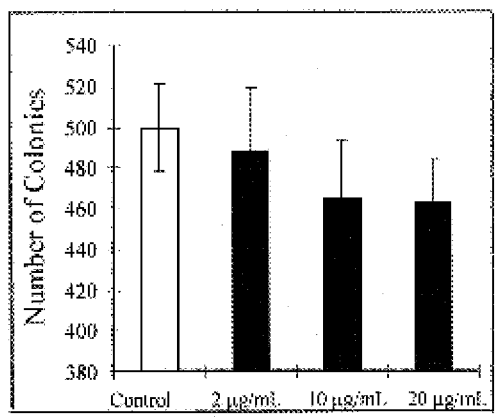
B
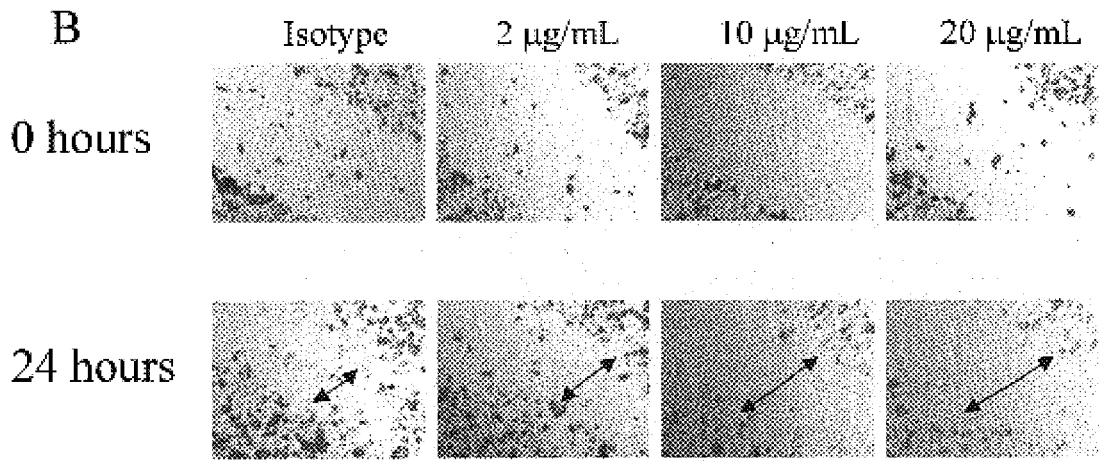
C
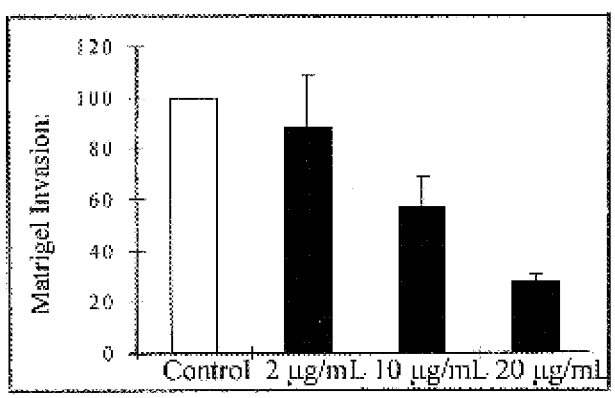

FIGURE 10
A
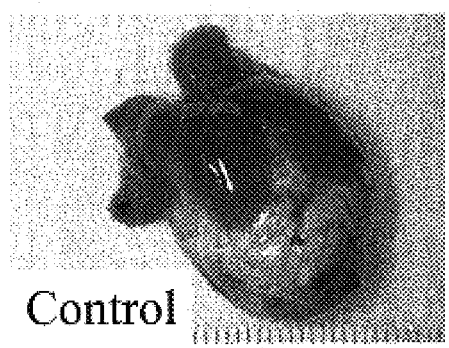
Control
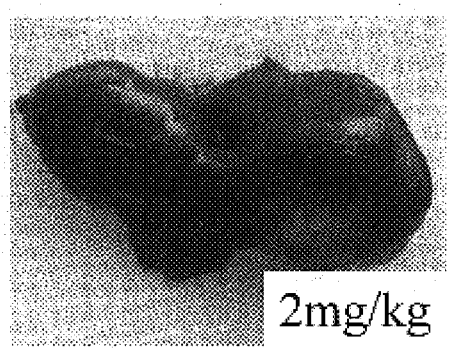
2mg/kg
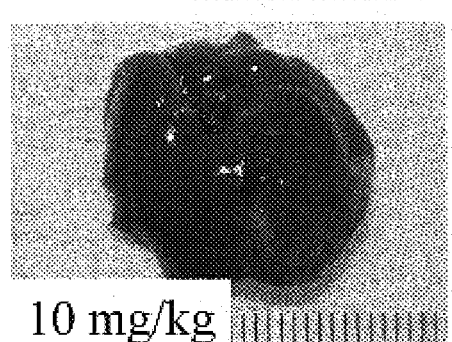
10 mg/kg
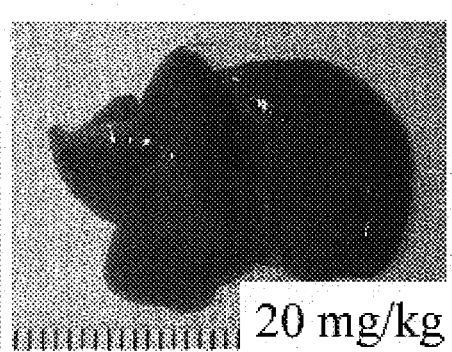
20 mg/kg
B
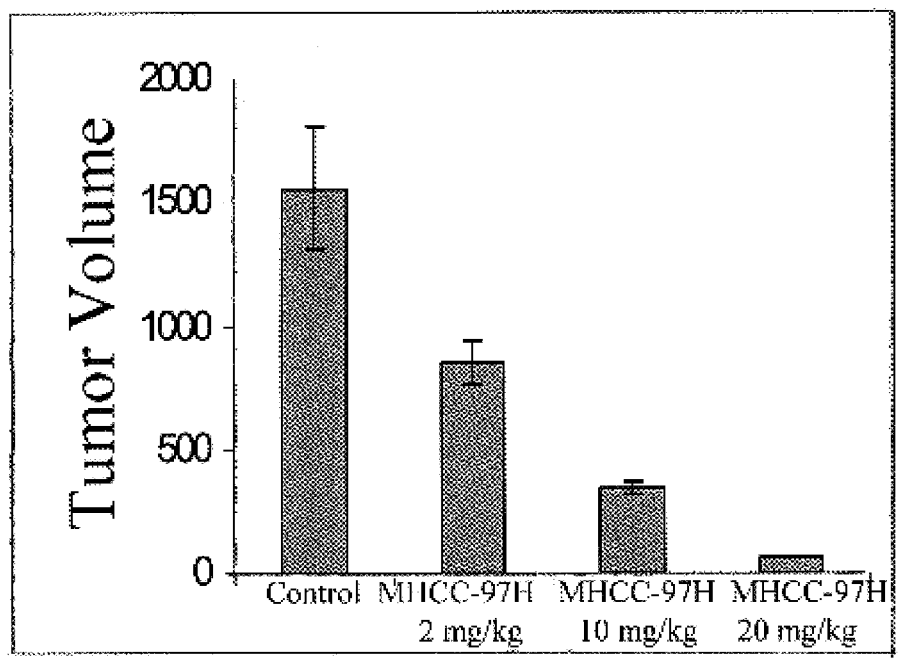

FIGURE 12
A
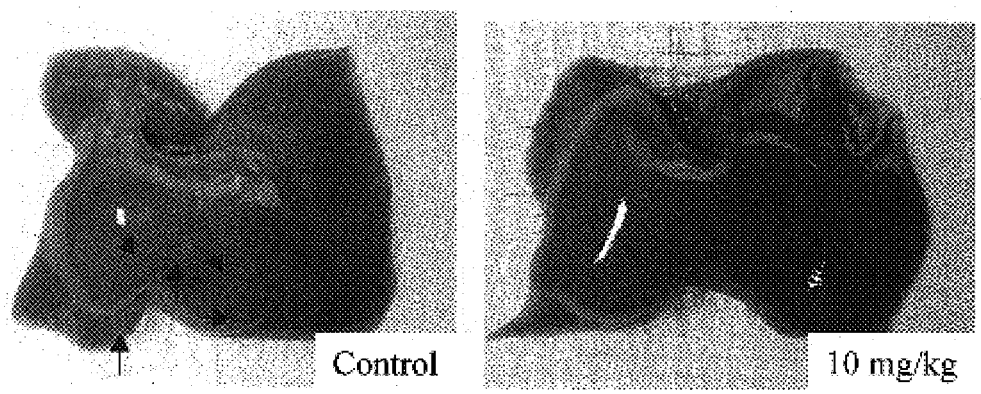
Control     10 mg/kg
B
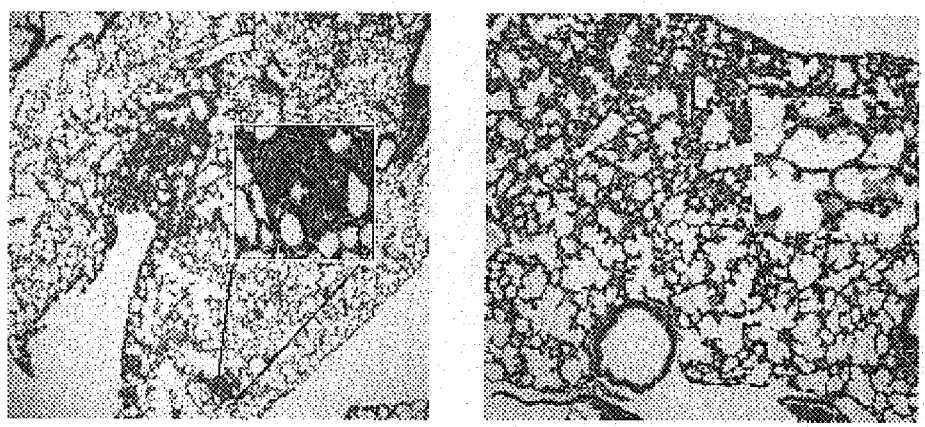
C
|  | Control | 5 mg/kg | 10 mg/kg |
|---|---|---|---|
| Liver metastasis | 5/5=100% | 1/5=20% | 0/5=0% |
| Lung metastasis | 5/5=100% | 0/5=0% | 0/5=0% |

CYTOTOXICITY MEDIATION OF CELLS EVIDENCING SURFACE EXPRESSION OF CD63

REFERENCE TO RELATED APPLICATIONS

This application is a continuation-in-part to U.S. patent application Ser. No. 11/321,624, filed on Dec. 29, 2005 now U.S. Pat. No. 7,431,923, and is a continuation-in-part to U.S. patent application Ser. No. 10/810,751, filed Mar. 26, 2004 now U.S. Pat. No. 7,361,343, which is a continuation-in-part to U.S. patent application Ser. No. 10/603,006, filed Jun. 23, 2003, which is a continuation-in-part to U.S. patent application Ser. No. 10/348,231, filed Jan. 21, 2003 now U.S. Pat. No. 7,009,040 (including U.S. divisional application Ser. No. 10/891,866, filed Jul. 15, 2004), and is a continuation-in-part to U.S. patent application Ser. No. 09/727,361 filed Nov. 29, 2000 now U.S. Pat. No. 6,657,048 issued Dec. 2, 2003 (including U.S. divisional application Ser. No. 10/713,642, filed Nov. 13, 2003), the contents of each of which are herein incorporated by reference.

FIELD OF THE INVENTION

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays, which utilize the CDMAB of the instant invention

BACKGROUND OF THE INVENTION

CD63 in Cancer: CD63 is a Type III membrane protein of the tetraspanin family whose 30 current members are characterized by the presence of four transmembrane segments. Several groups independently identified CD63, using antibodies raised to whole cell preparations of activated platelets, granulocytes, and melanoma cells. Cloning of the respective cDNAs of their cognate glycoprotein antigens led to the recognition that the different antigens were one and the same molecule. The Sixth International Workshop on Leukocyte Typing (1996) subsequently categorized these antibodies as CD63 antibodies. Prior to the 1996 Workshop, CD63 was known by multiple names (melanoma 1 antigen, ocular melanoma-associated antigen, melanoma associated antigen ME491, lysosome-associated membrane glycoprotein 3, granulophysin, melanoma-associated antigen MLA1), which were sometimes related to the antibodies that led to its partial characterization and identification. Thus, CD63 was also designated as antigen ME491 (MAb ME491), neuroglandular antigen (MAbs LS59, LS62, LS76, LS113, LS140 and LS152), Pltgp40 (MAbs H5C6, H4F8 and H5D2), human bone marrow stromal cell antigen (MAb 12F12), osteoprogenitor-specific marker (MAb HOP-26), and integrin-associated protein (MAb 6H1). Other antibodies that were found to cross react with human CD63 were 8-1H, 8-2A (cross-reactivity with ME491), NKI/C-3 and NKI/black-13 (Vennegoor et al. *Int J Cancer* 35(3):287-95 (1985); Vennegoor and Rumke, *Cancer Immunol Immunother.* 23(2):93-100 (1986); Demetrick et al., *J Natl Cancer Inst* 84(6):422-9 (1992); Wang et al., *Arch Ophthalmol.* 110(3):399-404 (1992)). Work with the rabbit polyclonal antibody RaC3, raised against the immunoaffinity-purified NKI/C3 antigen, revealed the target protein as a core polypeptide with an apparent molecular weight around 20 kDa and heavily post-translationally modified by N-linked carbohydrate (Gruters et al., *Cancer Res* 49(2):459-65 (1989)).

CD63 was initially cloned from a melanoma cDNA library using MAb ME491, one of a number of antibodies raised against a preparation the SK Mel 23 human cutaneous melanoma cell line and screened for binding to melanoma cells. Immunoprecipitation from $^{125}$I-lactoperoxidase-labelled melanoma cells revealed a 30-60 kDa protein present at the cell surface. The antigen recognized by this antibody was shown to be a protein highly post-translationally modified. By immunohistochemistry the antibody was found to recognize melanoma cells in tumor tissue but not the surrounding normal looking cells, thus suggesting that it recognized a potentially tumor-specific antigen determinant (Atkinson et al., *Hybridoma* 4, 243-255 (1984)). This antibody also stained melanoma cells in 87% of uveal melanoma cases and balloon cells in 86% of the cases where the latter were present. In this study staining of the normal occular tissue was variable, and positive in only a few of the normal cases and only rarely in the morphologically normal melanocytes (Folberg et al., *Arch Ophthalmol* 103(2):275-9 (1985)). In a separate experiment monoclonal antibodies MAb6-F1, MAb8-1H and MAb8-2A, raised also against the SK Mel 23 cell line, were shown to recognize the same antigen and to display an immunohistochemical staining pattern very similar to that obtained with MAb ME491. In addition these antibodies stained liver metastatic tumor tissue, in patients with primary choroidal melanoma but did not stain normal hepatocytes. In another study of human melanoma biopsies it was shown that the reactivity of MAb ME491 appeared to be inversely correlated with melanoma progression. The reactivity of the ME491 antibody was low in normal melanocytes, higher in the early stages of melanoma progression (dysplastic nevi and radial growth phase (RGP) tumors) and decreased or even absent in more advanced melanoma tumors such as those in the vertical growth phase (VGP) and in metastatic tumors. Another monoclonal antibody (MAb 4A3) raised against primary human uveal melanoma cells was found to specifically recognize an antigen present in these cells, and revealed only background levels of binding to lymphocytes from healthy individuals. The antigen(s) detected by this antibody, by Western immunoblotting of melanoma tissue, consist(s) of a doublet with an approximate apparent molecular weight of 55 kDa, suggesting that the antigen recognized by this antibody was not the same as that recognized by the antibodies that were clustered as anti-CD63 (Damato et al., *Invest Ophthalmol Vis Sci* 27(9):1362-7 (1986)).

CD63 was also found and partially characterized in human platelets using monoclonal antibodies raised against thrombin-activated platelets (MAbs 2.28, 2.19, 5.15 and 5d10). These antibodies detected an activation-dependent platelet membrane 53 kDa glycoprotein, as demonstrated by the increased number of binding sites (more than 10 fold) upon thrombin activation. In competition assays these antibodies blocked each other binding, suggesting that they recognized the same or spatially close antigen determinants. Results from platelet aggregation experiments revealed that these antibodies per se did not cause platelet aggregation, nor did they interfere with the aggregation induced by adenosine di-phosphate (ADP), thrombin, collagen, ristocetin and epinephrin. Electron microscopy data suggested that in resting platelets these antibodies recognized an antigen localized in lysosome membranes. Immunohistochemistry data indicated that these antibodies recognized an antigen present in restricted regions of spleen, lymph nodes, thymus and in endothelial cells. In another study the MAb 2.28 also labelled internal granules in resting platelets and in megakaryocytes and endothelial cells, and in the latter two it co-localized with antibodies to the enzyme cathepsin D, a known marker of lysosomal compartments. Follow up studies with antibody clustering and expression cloning, led to the identification of the antigen recognized by this antibody as CD63, and further confirmed its presence in lysosomal compartments, where it co-localized with the compartment-specific markers LAMP-1 and LAMP-2. Cloning of this molecule identified it as CD63 and allowed its inclusion in the tetraspanin family.

Expression of CD63 was detected in many different tissues and cell types. At the cellular level it was found to be associated with the plasma membrane and also with intracellular late endosomal vesicular structures. Cell activation led, in certain cases, to increased surface expression by mobilization of intracellular stores of CD63. CD63 was also found to co-localize, and physically associate, with MHC class II in B-lymphocytes, particularly in endosomes, in exosomes involved in exporting MHC class II complexes to the surface, and in secreted vesicles. CD63 was found to interact with other members of the tetraspanin family, such as CD9, CD81, CD111 (integrin chain $\alpha_{M,L,X}$), CD18 (integrin chain $\beta_2$), CD49c (VLA-3 or integrin chain $\alpha_3$), CD49d (integrin chain $\alpha_4$), CD49f (VLA-6 or integrin chain $\alpha_6$) and CD29 (integrin chain $\beta_1$), in a variety of cell types including B- and T-lymphocytes, neutrophils, breast cancer and melanoma cells.

The role of CD63 in cancer has been unclear. Although CD63 was initially discovered by several independent groups to be involved in diverse events such as platelet and granulocyte activation, MHC class II-dependent antigen presentation, integrin-dependent cell adhesion and motility, and tumor progression in certain types of cancers, its function has yet to be fully elucidated. Even though current evidence supports its role in a variety of cellular physiological events, it is not clear if these functions are independent of each other or if there is an underlying common cellular mechanism in which CD63 is involved.

Several groups have investigated the association between CD63 and the progression of certain types of tumors, particularly melanomas. A number of other anti-CD63 monoclonal antibodies, in addition to Mab ME491, were developed for immunohistochemical (IHC) staining of cancer samples obtained from patients with tumors at various stages of progression. It was observed that decreased staining, interpreted by the authors as most likely reflecting decreased expression of CD63, correlated with advanced progression and with metastatic characteristics of the tumors. A more recent study, also described a significant correlation between the apparent decreased expression levels (after quantitation of mRNA) of several members of the tetraspanin protein family, including CD63, and the in vitro invasiveness of several mammary carcinoma-derived cell lines. Another study identified CD63, by differential display, in cultured breast cancer cells subjected to estrogen deprivation. This indicated that CD63 expression can be steroid-hormone regulated and that altered CD63 abundance and/or function might also be associated with breast tumor progression.

By contrast, work with anti-CD63 monoclonal antibody MAb FC-5.01 revealed that its reactive epitope was variably expressed in different normal tissues. Although this antibody was found to recognize CD63, it did not distinguish between early and more advanced stage melanomas, including metastatic melanomas (unlike MAb ME491), which suggested that the CD63 antigen was present in these more advanced tumors, but that some of its epitopes may have been masked in the cells from tumors at different stages. This might have been due to altered post-translational modifications of the core CD63 polypeptide, or to the interaction of CD63 with other molecules, which might have affected the availability of specific epitopes for antibody recognition and binding. These results supported the observation, described by Si and Hersey, *Int J Cancer* 54(1):37-43 (1993), that staining with the anti-CD63 MAb NKI-C3, did not distinguish between tissue sections from melanomas at different stages of progression, such as primary, radial growth phase, vertical growth phase, and metastatic melanomas. Although in other studies (Adachi et al., *J Clin Oncol* 16(4): 1397-406 (1998); Huang et al., *Am J Pathol* 153(3):973-83 (1998)) analysis of mRNA from breast, and from non-small-cell lung cancers, by quantitative PCR, revealed that for two tetraspanin family members (CD9 and CD82) there was a significant correlation between their expression levels and tumor progression and patient prognosis, no such correlation was found for CD63, in that its expression was similar in all the samples. As a result of these, apparently conflicting, results, there is lack of strong and consistent data that would definitively demonstrate the association of CD63 with cancer.

To date very few in vivo studies have attempted to establish a link between CD63 and an eventual tumor suppressor function of this molecule. In one of these studies, human CD63-overexpressing H-ras-transformed NIH-3T3 cells, injected both subcutaneously and intraperitoneally into athymic mice, revealed a decreased malignant/tumorigenic phenotype, as indicated by decreased tumor size and metastatic potential as well as by increased survival time, when compared to the behavior of the parental non-CD63-overexpressing cells. This suggested that the presence of human CD63 in the transformed cells might suppress their malignant behavior. More recently, work with a transgenic mouse model expressing human CD63, and developed to induce tolerance to CD63, indicated that tumor growth of an injected human CD63-MHC class I (H-2K$^b$) co-transfected murine melanoma cell line could be inhibited, and survival increased, upon immunization with human CD63 fused to vaccinia virus. It was suggested by the authors that the therapeutic effect was T-lymphocyte-dependent, and that endogenous anti-CD63 antibodies did not appear to be involved in this protective effect, since tumor growth inhibition only occurred when animals were injected with the CD63-MHC class I co-transfected cells and not with the CD63-only transfected cell line. This interpretation was supported by the fact that in wild type animals, pre-immunized with purified human CD63 and shown to have developed anti-human CD63 antibodies, there was no protective effect against tumor cell growth. Work described by Radford et al., *Int J Cancer* 62(5):631-5 (1995) using the KM3 cell line, initially thought to be of human origin but later characterized as being of rat lineage, transfected with human CD63, suggested that expression of this protein decreased the growth and metastastic potential of these cells, relative to that observed using the parental non-transfected KM3 cells, when injected intradermally into athymic mice, although there was no significant difference between the in vitro growth rates of the various transfected and non-transfected cell lines. These observations distinguished the potential effect of CD63 from that of other tumor suppressor genes known to affect both the in vivo and the in vitro growth rates of tumor cells. Furthermore, addition of the anti-CD63 monoclonal antibody ME491, which was found to have a functional effect on the same cells by decreasing their random motility in an in vitro assay (Radford et al., *J Immunol* 158(7):3353-8 (1997)), did not impact their in vitro growth rates.

This study also described the observation that CD63 may promote migration in response to extracellular matrix (ECM)-derived chemoattractants, such as laminin, fibronectin, collagen and vitronectin, and that this effect may be mediated by the functional involvement of $\beta_1$-type integrins, although antibodies to the integrins were unable to block these effects. However, there appeared to be an antagonistic effect between the role of vitronectin-mediated signaling (a known ligand for the integrin $\alpha_v\beta_5$) and that of the signaling mediated by other ECM components such as fibronectin, laminin and collagen on CD63 transfected cells. This suggested that under specific conditions, in the presence of ECM components, expression of CD63 may lead to decreased migration, and that this may be dependent on a fine balance between adhesion and motility. In another study, an anti-CD63 monoclonal antibody (MAb 710F) enhanced the adhesion and spreading of PMA-treated HL-60 cells, while another anti-CD63 monoclonal antibody (MAb 2.28), promoted a similar effect, but only on a much smaller fraction of the cell population, and only when added in much larger amounts. These results showed that although many antibodies to CD63 have been developed, their functional effects can be quite different.

Tetraspanins may also be involved in cell proliferation. Oren et al. *Mol Cell Biol* 10(8):4007-15 (1990) described anti-proliferative effects of the murine MAb 5A6, that recognizes CD81 (TAPA-1), on lymphoma cell lines. In another study, ligation of CD37 in human T-lymphocytes with antibodies blocked CD37-induced proliferation. More recently, a study with an animal model deficient in the expression of CD37 (CD37 knockout) revealed that T lymphocytes from this animal were hyperproliferative compared to those from wild type animals in response to concanavalin A activation and CD3/T cell receptor engagement. It was therefore proposed that a functional role in cell growth and proliferation might be a common feature of the tetraspanin family. Recent studies with hepatoblastoma and hepatocellular carcinoma cells revealed that engagement of these cells with anti-CD81 monoclonal antibodies led to activation of the Erk/MAP kinase pathway. This signaling pathway has been shown to be involved with cell growth and proliferation events. In parallel work, transfected cell lines overexpressing human CD81 displayed increased proliferation relative to the mock-transfected control cells. Therefore, available evidence has pointed to a role of the tetraspanins in general, and of CD63 in particular, in events associated with cell growth proliferation and with cell adhesion/motility. These two types of cellular events are currently the target of intense research as both play a central role in tumor progression and metastasis.

Amino acid sequence determination and analysis did not reveal homology between tetraspanins and other protein families, or with any previously characterized functional modules, nor has it suggested any previously known enzymatic activity. As a result it has been very difficult to investigate the role of this family of proteins in the modulation of signal transduction pathways. However, the evidence generated using tetraspanin-specific reagents that led to changes in cellular physiology, and which were intimately dependent on the modulation of signal transduction pathways, suggests that tetraspanins have signal transduction properties. CD63 was shown to associate, both physically and functionally, with a number of molecules that are themselves either enzymes involved in the generation of secondary messenger signals, or are associated physically and/or functionally with such enzymes.

Experiments designed to dissect the mechanism controlling the interaction of human neutrophils with endothelial cells, which is one of the initial steps of the inflammatory response, revealed that pre-treatment of neutrophils with several anti-CD63 monoclonal antibodies (AHN-16, AHN-16.1, AHN-16.2, AHN-16.3 and AHN-16-5) promoted their adhesion to cultured endothelial cell layers. Furthermore this effect was strongly dependent on the presence of calcium ion ($Ca^{2+}$), a well-known modulator of many intracellular signaling pathways and which was restricted to a specific period of time during which the cells were exposed to the stimulating antibodies. After longer exposure to the antibody, adhesion of the neutrophils to the endothelial cells became insensitive to the later addition of $Ca^{2+}$, therefore implicating a dynamic and temporally regulated (transitory) event. In addition, CD63 was found to physically interact with the CD11/CD18 protein complex, and reagents that specifically targeted this complex mediated a modulatory signal. In this study CD63 was also found to be physically associated with, or to be part of, a complex that included the enzyme tyrosine kinases Lck and Hck. These enzymes are members of a class of proteins that play a central role in mediating intracellular regulatory signals upon activation of specific surface receptors and are part of cascades of signaling pathways that result in cell-specific physiological changes. Another study suggested that co-ligation of tetraspanins (including CD63) with monoclonal antibodies could enhance the phosphorylation or activity of the enzyme focal adhesion kinase (FAK) that was induced by adhesion of MDA-MB-231 breast cancer cells to collagen substrate. This pointed to a direct involvement of CD63 (and of other tetraspanin family members) in the modulation of integrin-mediated tyrosine kinase signaling pathways. Other signaling pathways that may functionally intersect with the presence and ligation of surface CD63 by the anti-CD63 monoclonal antibody MAb 710F appear to be those dependent on modulation of phosphorylation by the enzyme protein kinase C (PKC), another well known modulator of intracellular signaling pathways. In this context, enhancement of adhesion and of morphological changes in the myeloid cell line HL-60 by MAb 710F was dependent on pre-treatment of the cells with phorbol myristate acetate (PMA) although the temporal involvement of PKC was not conclusively demonstrated. However, later work by an independent group demonstrated that PMA-induced HL-60 differentiation was PKC-activity dependent since the molecule Ro31-8220, a specific inhibitor of this enzyme, blocked the effect of PMA.

Further evidence supporting the association of CD63, and other tetraspanin family members, with signal transduction pathways, arose from work that described a physical association, either direct or as part of a supramolecular complex, between CD63 (and also CD53) molecules with tyrosine phosphatase activity. In this study, immunoprecipitate complexes isolated with anti-CD63 antibodies were shown to be associated with tyrosine phosphatase activity, although unlike for CD53, which was shown to associate with the tyrosine phosphatase CD45, it was not possible to identify the CD63-associated phosphatase. More recently several members of the tetraspanin family were also found to be associated with a type II phosphatidylinositol 4-kinase (type II PI 4-K) (Berditchevski et al., *J Biol Chem* 272(5):2595-8 (1997)). This interaction appeared to be very specific since it was only identified for CD9, CD63, CD81, CD151 and A15/TALLA, and it was not observed to occur with CD37, CD52, CD82, or NAG-2. In addition, the association between tetraspanin family members and PI-4K was mutually exclusive since each PI-4 kinase-containing complex was limited to a single tetraspanin family member. CD63-PI-4 kinase complexes, in particular, were found, almost entirely, in intracellular compartments in lipid raft-like domains, unlike those formed with the other tetraspanin members. This observation suggested that this CD63 fraction, found to interact with the PI-4 kinase, might have been involved in specific intracellular events (Claas et al., *J Biol Chem* 276(11):7974-84 (2001)) related to, or dependent from, phosphoinositide biosynthesis pathways, which are well known for their involvement in the regulation of membrane trafficking (endocytosis and exocytosis) and of cytoskeleton reorganization, in addition to their function as secondary messenger molecules (Martin *Annu. Rev. Cell. Dev Biol* 14:231-64 (1998)).

The direct and important involvement of all the enzymes, that CD63 was found until now to be directly associated with, in the regulation of signaling pathways provided further evidence in support of the association of CD63 with the modulation of signal transduction pathways, either as a regulator or as an effector molecule downstream from the activity of these enzymes.

Elucidation of the mechanisms that lead to tumor progression is a very difficult and complex endeavor frequently marked by apparently contradictory observations and, as a result, it is rare that those observations successfully translate into effective therapies. In view of what is currently known about the association of CD63 with tumor progression and metastasis and with signal transduction mechanisms, it is possible that its function may be altered, in tumor cells.

Development of antigen-specific reagents with cytotoxic effects on tumor cells, that bind cells expressing the recognized antigen(s) and which by themselves, or associated with other molecules, have cellular and in vivo physiological activity such that these reagents inhibit tumor cell growth, progression and metastasis, without significant deleterious effects on normal cell populations, would be extremely beneficial as a potential therapeutic and or diagnostic tool.

Recently, new data has pointed to an important mode of action of CD63 in the regulation of normal cell physiology, and that when altered may have important impact on the behavior of the cells under pathological conditions, including in cancer.

MAb antibody Fc-5.01, known to cause internalization of CD63 in breast cancer cells was used to determine the levels of surface expression and internalization of CD63 in human dendritic cells (DCs) (Mantezazza et al., *Blood* 104(4):1183-90 (2004)). CD63 was found to localize both at the cell surface and intracellularly, in co-localization with endosomal and lysosomal markers. The intact antibody, and its Fab fragments were able to induce internalization of CD63. Simultaneously internalization of CD63 promoted by Fc-5.01 resulted in decreased surface expression of several integrin molecules, CD11b, CD18, CD29 and α5, but not of β3 or of HLA-II molecules. Results from a chemotaxis assay revealed that this antibody, and others that recognize other members of the tetraspanin family of proteins, caused an increase in the number of cells that migrated across a membrane barrier towards chemoattractants. In these cells (immature DCs) yeast phagocytosis, which is mediated by β1,3-glycan receptors was accompanied by a decrease in the levels of cell surface CD63 but not of the tetraspanins CD9, CD81 and CD82, nor of HLA-II molecules. On the other hand, internalization induced by Dextran-FITC, which is mediated by the macrophage mannose receptor (MMR) did not result in decreased CD63 surface expression or of CD9, CD81, CD82, HLA-I and HLA-II molecules. Therefore it would appear that CD63 is associated with specific receptors, sometimes physically as in the case of the β1,3-glycan receptor dectin-1, and participate in the internalization events. The fact that the surface expression of several integrin molecules is decreased upon antibody-induced internalization of CD63 also suggests that such a CD63-dependent event can have a significant impact on the cell surface receptor composition and thus impact the physiology of such cell populations as demonstrated by the effect on the DC migration assay.

In another study, the internalization of membrane type-1 metalloproteinase (MT1-MMP) was found to be affected by CD63. In this study FLAG-tagged MT1-MMP internalized and acquired a diffuse cytoplasmic distribution that was accompanied by a decrease in its cell surface levels. Addition of chlorquine, a known lysosomal proteinase inhibitor, partially inhibited this internalization-dependent disappearance of cell surface MT1-MMP, and simultaneously altered the internalization-dependent cytoplasmic distribution in such a way that MT1-MMP remained associated with CD63 positive internal granule-type structures. Co-transfection of cells with MT1-MMP and CD63 resulted in decreased cell surface levels of this metalloprotease, which was not dependent on the overall levels of MMP activity, since an inhibitor of these molecules, BB94, did not have any impact on this decrease, while chlorquine did. This observation suggested that increased CD63 expression may accelerate the turnover/internalization/degradation of MT1-MMP. The increased internalization/degradation of MT1-MMP depended on the direct interaction between MT1-MMP and CD63. This type of function was further supported by previous observations that CD63 directly interacted with the μ2 and μ3 subunbits of the adaptor proteins AP-2 and AP-3 respectively and which are involved in protein sorting to endosomes and lysosomes. It was also previously shown that the cytoplasmic tail of MT1-MMP was important for the internalization of this molecule and that this event played an important role in the regulation of its invasion-promoting activity. MT1-MMP is also considered to play important roles in the invasion of malignant tumor cells. Therefore it is possible that regulation of its overall levels may depend on its interaction and internalization by associating with CD63.

In another recent publication (Xu et al., *Embo J* 23(4):811-22 (2004)) a genetic screen for *Drosophila* eye-enriched genes that might be involved in retinal degeneration identified a large number of genes among which that of a tetraspanin-like molecule named 'sunglasses' ('sun'). The closest-related mammalian protein was the tetraspanin CD63. And similarly to CD63, 'sun' was found to be enriched in lysosomes, as suggested by immunoelectron microscopy. Results from this work suggested that 'sun' participates in the normal down-regulation of Rh1 signaling, independent of the arrestin mediated mechanism that is typical of other G-protein coupled receptors. In addition 'sun' was important not only in the regular turnover of activated Rh1 but also, and possibly dependent on this event, had a significant impact in the maintenance of rhabdomers' structure, which resulted in a dramatic sun-dependent retinal degeneration in the mutant flies. Together the data implicates this homologue of mammalian CD63 in the normal trafficking-dependent turnover of proteins and abnormalities in its expression/function result in physiological abnormalities.

Another publication on the role of CD63 in receptor internalization described the co-localization of the β-subunit of the gastric ion pump H,K-ATPase with this tetraspanin in COS cells co-transfected with both molecules. In this study it was found also that the H,K-ATPase β-subunit underwent a CD63 expression-dependent enhancement of internalization and of localization to lysosome-like cytoplasmic granular structures.

All the data from the work described above suggested that CD63 was also involved in the normal turnover of cell-surface molecules, by participating in their internalization and lysosomal-dependent degradation, thus participating in the control of the normal cell physiology. It is possible, therefore, that manipulation of this function of CD63 might be an important tool to control events dependent on the activity of specific molecules, or groups of molecules, whose surface expression or function is either altered or contributes to abnormal cell behavior in pathological conditions such as cancer.

Until now, no anti-CD63 antibodies, or other reagents that specifically targeted CD63-expressing cells, were reported and shown to have a simultaneous impact on the in vitro and on the in vivo growth characteristics of tumor cells, and also on the survival time of animal models of tumor cell growth.

Monoclonal Antibodies as Cancer Therapy: Each individual who presents with cancer is unique and has a cancer that is as different from other cancers as that person's identity. Despite this, current therapy treats all patients with the same type of cancer, at the same stage, in the same way. At least 30 percent of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells. However, it is now widely recognized that no single monoclonal antibody can serve in all instances of cancer, and that monoclonal antibodies can be deployed, as a class, as targeted cancer treatments. Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-Her2/neu antibody (Herceptin®) in combination with cisplatin. In this trial 37 patients were assessed for responses of which about a quarter had a partial response rate and an additional quarter had minor or stable disease progression. The median time to progression among the responders was 8.4 months with median response duration of 5.3 months.

Herceptin® was approved in 1998 for first line use in combination with Taxol®. Clinical study results showed an increase in the median time to disease progression for those who received antibody therapy plus Taxol® (6.9 months) in comparison to the group that received Taxol® alone (3.0 months). There was also a slight increase in median survival; 22 versus 18 months for the Herceptin® plus Taxol® treatment arm versus the Taxol® treatment alone arm. In addition, there was an increase in the number of both complete (8 versus 2 percent) and partial responders (34 versus 15 percent) in the antibody plus Taxol® combination group in comparison to Taxol® alone. However, treatment with Herceptin® and Taxol® led to a higher incidence of cardiotoxicity in comparison to Taxol® treatment alone (13 versus 1 percent respectively). Also, Herceptin® therapy was only effective for patients who over express (as determined through immunohistochemistry (IHC) analysis) the human epidermal growth factor receptor 2 (Her2/neu), a receptor, which currently has no known function or biologically important ligand; approximately 25 percent of patients who have metastatic breast cancer. Therefore, there is still a large unmet need for patients with breast cancer. Even those who can benefit from Herceptin® treatment would still require chemotherapy and consequently would still have to deal with, at least to some degree, the side effects of this kind of treatment.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minor responses among 52 patients in protocols using additional cyclophosphamide. To date, Phase III clinical trials of 17-1A have not demonstrated improved efficacy as adjuvant therapy for stage III colon cancer. The use of a humanized murine monoclonal antibody initially approved for imaging also did not produce tumor regression.

Only recently have there been any positive results from colorectal cancer clinical studies with the use of monoclonal antibodies. In 2004, ERBITUX® was approved for the second line treatment of patients with EGFR-expressing metastatic colorectal cancer who are refractory to irinotecan-based chemotherapy. Results from both a two-arm Phase II clinical study and a single arm study showed that ERBITUX® in combination with irinotecan had a response rate of 23 and 15 percent respectively with a median time to disease progression of 4.1 and 6.5 months respectively. Results from the same two-arm Phase II clinical study and another single arm study showed that treatment with ERBITUX® alone resulted in an 11 and 9 percent response rate respectively with a median time to disease progression of 1.5 and 4.2 months respectively.

Consequently in both Switzerland and the United States, ERBITUX® treatment in combination with irinotecan, and in the United States, ERBITUX® treatment alone, has been approved as a second line treatment of colon cancer patients who have failed first line irinotecan therapy. Therefore, like Herceptin®, treatment in Switzerland is only approved as a combination of monoclonal antibody and chemotherapy. In addition, treatment in both Switzerland and the US is only approved for patients as a second line therapy. Also, in 2004, AVASTIN® was approved for use in combination with intravenous 5-fluorouracil-based chemotherapy as a first line treatment of metastatic colorectal cancer. Phase III clinical study results demonstrated a prolongation in the median survival of patients treated with AVASTIN® plus 5-fluorouracil compared to patients treated with 5-fluorouracil alone (20 months versus 16 months respectively). However, again like Herceptin® and ERBITUX®, treatment is only approved as a combination of monoclonal antibody and chemotherapy.

There also continues to be poor results for lung, brain, ovarian, pancreatic, prostate, and stomach cancer. The most promising recent results for non-small cell lung cancer came from a Phase II clinical trial where treatment involved a monoclonal antibody (SGN-15; dox-BR96, anti-Sialyl-LeX) conjugated to the cell-killing drug doxorubicin in combination with the chemotherapeutic agent TAXOTERE®. TAXOTERE® is the only FDA approved chemotherapy for the second line treatment of lung cancer. Initial data indicate an improved overall survival compared to TAXOTERE® alone. Out of the 62 patients who were recruited for the study, two-thirds received SGN-15 in combination with TAXOTERE® while the remaining one-third received TAXOTERE® alone. For the patients receiving SGN-15 in combination with TAXOTERE®, median overall survival was 7.3 months in comparison to 5.9 months for patients receiving TAXOTERE® alone. Overall survival at 1 year and 18 months was 29 and 18 percent respectively for patients receiving SNG-15 plus TAXOTERE® compared to 24 and 8 percent respectively for patients receiving TAXOTERE® alone. Further clinical trials are planned.

Preclinically, there has been some limited success in the use of monoclonal antibodies for melanoma. Very few of these antibodies have reached clinical trials and to date none have been approved or demonstrated favorable results in Phase III clinical trials.

The discovery of new drugs to treat disease is hindered by the lack of identification of relevant targets among the products of 30,000 known genes that unambiguously contribute to disease pathogenesis. In oncology research, potential drug targets are often selected simply due to the fact that they are over-expressed in tumor cells. Targets thus identified are then screened for interaction with a multitude of compounds. In the case of potential antibody therapies, these candidate compounds are usually derived from traditional methods of monoclonal antibody generation according to the fundamental principles laid down by Kohler and Milstein (1975, Nature, 256, 495-497, Kohler and Milstein). Spleen cells are collected from mice immunized with antigen (e.g. whole cells, cell fractions, purified antigen) and fused with immortalized hybridoma partners. The resulting hybridomas are screened and selected for secretion of antibodies which bind most avidly to the target. Many therapeutic and diagnostic antibodies directed against cancer cells, including Herceptin® and RITUXIMAB, have been produced using these methods and selected on the basis of their affinity. The flaws in this strategy are twofold. Firstly, the choice of appropriate targets for therapeutic or diagnostic antibody binding is limited by the paucity of knowledge surrounding tissue specific carcinogenic processes and the resulting simplistic methods, such as selection by overexpression, by which these targets are identified. Secondly, the assumption that the drug molecule that binds to the receptor with the greatest affinity usually has the highest probability for initiating or inhibiting a signal may not always be the case.

Despite some progress with the treatment of breast and colon cancer, the identification and development of efficacious antibody therapies, either as single agents or co-treatments, has been inadequate for all types of cancer.

Prior Patents:

U.S. Pat. No. 5,296,348 teaches methods for selecting monoclonal antibodies specific for cancer cell surface antigens that are internalizing, and for identifying monoclonal antibodies having anti-transcriptional and/or anti-replicational effects on cell metabolism. By way of example the ME491 antibody was shown to internalize in W9, WM35, WM983 melanoma cells, and SW948 colorectal carcinoma cells. In addition ME491 antibody was shown to decrease transcription and cell proliferation in SW948 cells. The patent application US20030211498A1 (and its related applications: WO0175177A3, WO0175177A2, AU0153140A5) allege a method of inhibiting the growth or metastasis of an ovarian tumor with an antibody that binds an ovarian tumor marker polypeptide encoded by an ovarian tumor marker gene selected from among a group that includes CD63 antigen. Serial analysis of gene expression using ovarian cancer was carried out to identify ovarian tumor marker genes which lead to the identification of CD63 as a candidate. The patent application WO02055551A1 (and its related application CN1364803A) alleges a new polypeptide-human CD63 antigen 56.87. The patent application CN1326962A alleges a new polypeptide-human CD63 antigen 14.63. The patent application CN1326951A alleges a new polypeptide-human CD63 antigen 15.07. The patent application CN1351054A alleges a new polypeptide-human CD63 antigen 11.11. These patents and patent applications identify CD63 antigens and antibodies but fail to disclose the isolated monoclonal antibody of the instant invention, or the utility of the isolated monoclonal antibody of the instant invention.

The gene encoding the ME491 polypeptide antigen was cloned and the sequence was received for publication on Feb. 24, 1988 (Can Res 48:2955, 1988, Jun. 1); the gene encoding CD63 was cloned and the sequence published in February 1991 (JBC 266(5):3239-3245, 1991) and the publication clearly indicated the identity of ME491 with CD63.

WO2004041170.89 (Sequence ID No.: 89, priority filing date: 29 Jun. 2004), WO2003068268-A2 (Sequence ID No.: 1, priority filing date: 13 Feb. 2003 (2003WO-EP001461); other priority date: 14 Feb. 2002 (2002 GB-00003480)), WO2003057160-A29 (Sequence ID No.: 40, priority filing date: 30 Dec. 2002 (2002WO-US041798); other priority date: 2 Jan. 2002 (2002US-0345444P)) all allege polypeptides that have 100 percent sequence homology to CD63.

WO2003016475-A2 (Sequence ID No.: 9787& 12101, priority filing date: 14 Aug. 2002 (2002WO-US025765); other priority date: 14 Aug. 2001 (2001 US-0312147P) allege polypeptides that have 100 percent sequence homology with 237 amino acids of 238 amino acids comprising CD63.

WO2003070902-A2 (Sequence ID No.:27, priority filing date: 18 Feb. 2003 (2003WO-US004902); other priority date: 20 Feb. 2002 (2002US-0358279P)) allege polypeptides that have 94 percent sequence homology with 224 amino acids of 238 amino acids comprising CD63.

EP1033401-A2 (Sequence ID No.: 4168& 4913, priority filing date: 21 Feb. 2000 (2000EP-00200610); other priority date: 26 Feb. 1999 (99US-0122487P)) allege polypeptides that have 100 percent sequence homology with 205 amino acids and with 94 amino acids of 238 amino acids comprising CD63, respectively.

WO200257303-A2 (Human prey protein for *Shigella* ospG#26, priority filing date: 11 Jan. 2002 (2002WO-EP000777); other priority date: 12 Jan. 2001 (2001US-0261130P)) allege polypeptides that have 100 percent sequence homology with 130 amino acids of 238 amino acids comprising CD63.

WO200055180-A2 (Sequence ID No.: 756, priority filing date: 08 Mar. 2000 (2000WO-US005918); other priority date: 12 Mar. 1999 (99US-0124270P)) allege polypeptides that have 99 percent sequence homology with 127 amino acids of 238 amino acids comprising CD63.

WO200200677-A1 (Sequence ID No.:3203, priority filing date: 07 Jun. 2001 (2001WO-US018569); other priority date: 7 Jun. 2000 (2000US-0209467P)) allege polypeptides that have 97 percent sequence homology with 132 amino acids of 238 amino acids comprising CD63.

WO9966027-A1 (Large extracellular loop sequence from human CD63 protein, priority filing date: 15 Jun. 1999 (99WO-US013480); other priority date: 15 Jun. 1998 (98US-0089226P)) allege polypeptides that have 100 percent sequence homology with 99 amino acids of 238 amino acids comprising CD63.

WO200270539-A2 (Sequence ID No.: 1207, priority filing date: 5 Mar. 2002 (2002WO-US005095); other priority date: 5 Mar. 2001 (2001 US-00799451)) allege polypeptides that have 86 percent sequence homology with 102 amino acids of 238 amino acids comprising CD63.

EP1033401-A2 (Sequence ID No.: 4169, 21 Feb. 2000 (2000EP-00200610); other priority date: 26 Feb. 1999 (99US-0122487P)) allege polypeptides that have 100 percent sequence homology with 74 amino acids of 238 amino acids comprising CD63.

These patent applications identify polypeptides that have varying sequence homology to CD63 antigen. In most cases these application also allege antibodies and antibody derivatives to the corresponding polypepide and their homologs but fail to disclose the isolated monoclonal antibody of the instant invention, or the utility of the isolated monoclonal antibody of the instant invention for the treatment of human lung, prostate and colon cancer or other human cancers. Importantly, all the above applications were filed after the publication of the sequence of the polynucleotide encoding CD63.

SUMMARY OF THE INVENTION

This application utilizes the method for producing patient specific anti-cancer antibodies as taught in the U.S. Pat. No. 6,180,357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases. These antibodies can also be used for the prevention of cancer by way of prophylactic treatment. Unlike antibodies generated according to traditional drug discovery paradigms, antibodies generated in this way may target molecules and pathways not previously shown to be integral to the growth and/or survival of malignant tissue. Furthermore, the binding affinities of these antibodies are suited to requirements for initiation of the cytotoxic events that may not be amenable to stronger affinity interactions. Also, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming an antibody conjugate.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and an anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity or complement dependent cytotoxicity. For example murine IgM and IgG2a antibodies can activate human complement by binding the C1 component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are three additional mechanisms of antibody-mediated cancer cell killing. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost. The third is the effect of such antibodies on direct ligation of cell surface moieties that may lead to direct cell death, such as ligation of death receptors such as TRAIL R1 or TRAIL R2, or integrin molecules such as alpha V beta 3 and the like.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

Using substantially the process of U.S. Pat. No. 6,180,357, and as disclosed in U.S. Pat. No. 7,009,040, the contents of each of which are herein incorporated by reference, the mouse monoclonal antibody 7BD-33-11A was obtained following immunization of mice with cells from a patient's breast tumor biopsy. The 7BD-33-11A antigen is expressed on the cell surface of a wide range of human cell lines from different tissue origins. The breast cancer cell line MCF-7 and prostate cancer cell line PC-3 were susceptible to the cytotoxic effects of 7BD-33-11A in vitro.

The result of 7BD-33-11A cytotoxicity against breast and prostate cancer cells in culture was further extended by its anti-tumor activity towards these cancer indications in vivo (as disclosed in U.S. Pat. No. 7,009,040, Ser. No. 10/603,006 and Ser. No. 10/810,751).

7BD-33-11A prevented tumor growth and tumor burden in a MB-231 preventative in vivo model of human breast cancer. Monitoring continued past 300 days post-treatment. Mice treated with 7BD-33-11A never developed tumors and 87.5 percent of the 7BD-33-11A-treatment group was still alive at over 9 months post-implantation (one of the mice died from non-tumor related causes). Conversely, the isotype control group had 100 percent mortality by day 72 (23 days post-treatment). Therefore 7BD-33-11A enhanced survival and prevented tumor growth (thus delaying disease progression) in a breast cancer model.

7BD-33-11A also significantly suppressed tumor growth and decreased tumor burden in an established in vivo model of human breast cancer. By day 80 (23 days post-treatment), 7BD-33-11A treated mice had 83 percent lower mean tumor volumes in comparison to the isotype control group (p=0.001). Using survival as a measure of antibody efficacy, it was estimated that the risk of dying in the 7BD-33-11A treatment group was about 16 percent of the isotype control group (p=0.0006) at around 60 days post-treatment. 100 percent of the isotype control group died by 50 days post-treatment. This data demonstrated that 7BD-33-11A treatment conferred a survival benefit and reduced tumor burden compared to the control treated group.

7BD-33-11A treatment appeared safe, as it did not induce any signs of toxicity, including reduced body weight and clinical distress. Thus, 7BD-33-11A and 1A245.6 treatment was efficacious as it both delayed tumor growth and enhanced survival compared to the control-treated group in a well-established model of human breast cancer.

In a study disclosed in pending application Ser. No. 10/810, 751, filed Mar. 26, 2004, the contents of which are herein incorporated by reference, the effect of 7BD-33-11A compared to chemotherapeutic drug (cisplatin) treatment alone or in combination was determined in two different established breast cancer xenograft models.

In the MB-231 model, at day 83 (20 days after treatment), 7BD-33-11A treatment resulted in an 83 percent reduction in tumor growth relative to the buffer control treated animals (p=0.002). Cisplatin treatment alone resulted in a 77 percent reduction in tumor size relative to the control, while cisplatin in combination with 7BD-33-11A resulted in an 88 percent reduction in tumor size relative to the control (p=0.006).

In the MDA-MB-468 (MB-468) model, at day 62 (12 days after treatment) the greatest reduction in tumor growth (97 percent, p=0.001) was observed with cisplatin treatment in combination with 7BD-33-11A. Cisplatin treatment alone produced a 95 percent decrease in tumor growth in comparison to the buffer control while 7BD-33-11A treatment alone showed a 37 percent (p=0.046) reduction.

In both the MB-231 and MB-468 model, treatment with 7BD-33-11A led to greater animal well-being in comparison to treatment with cisplatin as measured by body weight. These results indicated that 7BD-33-11A treatment had greater efficacy in comparison with cisplatin treatment alone in the MB-231 model and was better tolerated with fewer adverse effects, such as weight loss, than cisplatin in both breast cancer models.

To determine the effects of 7BD-33-11A treatment at various doses, a dose response experiment was performed in a preventative breast cancer xenograft model (as disclosed in Ser. No. 10/810,751). At day 55 (5 days after treatment), the 0.2 mg/kg treatment group had reduced tumor growth by 85 percent relative to the isotype control treated group. Also at day 55, both the 2 and 20 mg/kg treatment groups had yet to develop tumors. Similar results were obtained past day 125 (75 days after treatment), where the 20 mg/kg treatment group had still not developed tumors and the 2 mg/kg treatment group had some initial tumor growth. 7BD-33-11A treatment also demonstrated a survival benefit. All of the mice in the isotype control group had died by day 104 (54 days after treatment) while the 0.2 mg/kg 7BD-33-11A treatment group survived until day 197 (147 days after treatment). Even greater survival benefits were observed with the 2.0 and 20 mg/kg 7BD-33-11A treatment groups; only 50 percent of the 2.0 mg/kg treatment group had died by day 290 (240 days after treatment) while none of the 20 mg/kg treatment group had died by day 290. Therefore, 7BD-33-11A treatment showed significant tumor growth reduction and increased survival with all three doses with the greatest degree of efficacy being exhibited by the highest dose.

In addition to the beneficial effects in the established in vivo tumor model of breast cancer, 7BD-33-11A treatment also had anti-tumor activity against PC-3 cells in a preventative in vivo prostate cancer model (disclosed in Ser. No. 10/603,006 and Ser. No. 10/810,751, the contents of each of which are herein incorporated by reference). 7BD-33-11A and 1A245.6 treatment was significantly (p=0.001 and 0.017 respectively) more effective in suppressing tumor growth shortly after the treatment period than an isotype control antibody. At the end of the treatment phase, mice given 7BD-33-11A had tumors that grew to only 31 percent of the isotype control group.

For PC-3 SCID xenograft models, body weight can be used as a surrogate indicator of disease progression. On day 52, 7BD-33-11A treatment significantly (p=0.002) prevented the loss of body weight by 54 percent in comparison to isotype control. Mice were monitored for survival post-treatment. At 11 days post-treatment, isotype and buffer control mice had reached 100 percent mortality. Conversely, 7BD-33-11A reached 100 percent mortality at day 38 post-treatment, 3 times longer than the control groups. Thus, 7BD-33-11A treatment was efficacious as it both delayed tumor growth, prevented body weight loss and extended survival compared to the isotype control treated group in a well-established model of human prostate cancer.

In addition to the preventative in vivo tumor model of prostate cancer, 7BD-33-11A demonstrated anti-tumor activity against PC-3 cells in an established in vivo tumor model (disclosed in pending application Ser. No. 10/603,006, filed Jun. 23, 2003, and Ser. No. 10/810,751, the contents of each of which are herein incorporated by reference). Treatment with 7BD-33-11A was again compared to isotype control. It was shown that the 7BD-33-11A-treatment group had significantly (p<0.024) smaller mean tumor volumes compared with the isotype control treated group immediately following treatment. 7BD-33-11A treatment mediated tumor suppression by 36 percent compared to the isotype control group.

In addition to the beneficial effects in the in vivo tumor models of breast and prostate cancer, 7BD-33-11A treatment also had anti-tumor activity against BxPC-3 cells in a preventative in vivo pancreatic cancer model (as disclosed in Ser. No. 11/321,624). 7BD-33-11A treatment was significantly more effective in suppressing tumor growth (71 percent, p=0.0009) shortly after the treatment period than the buffer control. In addition, 7BD-33-11A treatment conferred a survival benefit in comparison to the buffer control treatment group. In the 7BD-33-11A treated group, 40 percent of the mice were still alive over 2 weeks after all of the buffer control group mice had died.

In addition to the beneficial effects in the in vivo tumor models of breast, prostate and pancreatic cancer, 7BD-33-11A treatment also had anti-tumor activity against A2058 and A375 cells in two separate preventative in vivo melanoma cancer models (as disclosed in Ser. No. 11/321,624). In both the A2058 and A375 model, 7BD-33-11A treatment was significantly more effective in suppressing tumor growth (72 percent, p=0.011 and 63 percent, p=0.0006 respectively) than the buffer control. The anti-tumor activities of 7BD-33-11A in melanoma as well as in breast, prostate and pancreatic cancer models make it an attractive anti-cancer therapeutic agent.

In addition to the beneficial effects demonstrated in the preventative in vivo model of human melanoma, 7BD-33-11A-treatment also had anti-tumor activity against A2058 and A375 cells in two separate established in vivo melanoma cancer models (as disclosed in pending application Ser. No. 11/321,624, filed Dec. 29, 2005). Tumor growth was significantly inhibited in the 7BD-33-11A-treatment and the 7BD-33-11A plus dacarbazine treatment group for the A2058 and A375 model respectively. In the A2058 model, the mean tumor volume was 30.87 percent (p<0.0443) of the control group measurement. In the A375 model, the 7BD-33-11A/dacarbazine combination treatment group resulted in a median TTE (time-to-endpoint) of 39.1 days, corresponding to a significant 147 percent delay in tumor growth (p<0.01). No toxic deaths were observed in either model. Therefore, 7BD-33-11A treatment appeared safe and has displayed efficacy in the treatment of breast and now melanoma in vivo models of established human cancer.

To determine if the efficacy demonstrated by 7BD-33-11A in vivo is due in whole or in part to ADCC activity, 7BD-33-11A anti-tumor activity was measured against MB-231 cells in an established tumor model in both NOD SCID and SCID mice (as disclosed in Ser. No. 11/321,624). NOD SCID mice are functionally deficit in natural killer (NK) cells and lack circulating complement and a functionally mature macrophage population while SCID mice have both complement and robust NK cell activity. 7BD-33-11A is a murine IgG2a monoclonal antibody and is therefore capable of ADCC activity in vivo. The anti-tumor activity of 7BD-33-11A was compared to both a buffer control and H460-22-1, a murine IgG1 monoclonal antibody that should not exhibit its activity through ADCC based on its isotype. On day 54 (4 days after the last treatment), in the SCID treated group, 7BD-33-11A and H460-22-1 treated mice developed tumors that were only 1.9 and 3.6 percent respectively of the mean tumor volume of the buffer control treated mice. Conversely, in the NOD SCID treated group, again on day 54 (4 days after the last treatment), 7BD-33-11A treated mice had tumor growth that was 67 percent of the mean tumor volume of the buffer control treated mice. H460-22-1 treated mice exhibited a similar effect as in the SCID mice; tumor growth was 1.4 percent of the mean tumor volume of the buffer control treated mice. Consequently, 7BD-33-11A activity in vivo seems to be in-part due to ADCC activity while H460-22-1's anti-tumor effect appears to be independent of ADCC.

In order to validate the 7BD-33-11A epitope as a drug target, the expression of its target antigen in normal human tissues was determined. As disclosed in Ser. No. 10/603,006 and Ser. No. 10/810,751, the contents of each of which are herein incorporated by reference, the binding of 7BD-33-11A towards normal human tissues was determined. By IHC staining, the majority of the tissues failed to express the 7BD-33-11A antigen, including the vital organs, such as the kidney, heart, and lung. 7BD-33-11A stained the salivary gland, liver, pancreas, stomach, prostate and duodenum, and strongly stained the tonsil. Results from tissue staining indicated that 7BD-33-11A showed restricted binding to various cell types but had binding to infiltrating macrophages, lymphocytes, and fibroblasts. 7BD-33-11A displayed both membrane and cytoplasmic staining patterns.

As disclosed in Ser. No. 10/810,751, the contents of which are herein incorporated by reference, 7BD-33-11A was compared with commercially available anti-CD63 antibodies (RFAC4 and H5C6). Results from normal human tissue staining indicated that 7BD-33-11A again showed restricted binding to various cell types but had binding to infiltrating macrophages, lymphocytes, and fibroblasts. The RFAC4 and H5C6 antibodies showed a similar staining pattern in comparison to each other. However, the staining pattern of both RFAC4 and H5C6 was quite different than that observed with 7BD-33-11A. Specifically, both RFAC4 and H5C6 antibodies bound to a broader range of normal tissues, usually had higher staining intensity in tissues where 7BD-33-11A was also positive and bound not only to infiltrating macrophages, lymphocytes and fibroblasts but also to the epithelium in a majority of the tissues.

Localization of the 7BD-33-11A antigen and determination of its prevalence within the population, such as among breast cancer patients, is important in assessing the therapeutic use of this antibody and designing effective clinical trials. To address 7BD-33-11A antigen expression in breast tumors from cancer patients, tumor tissue samples from 98 individual breast cancer patients were screened for expression of the 7BD-33-11A antigen (results from 50 patients have been previously described in Ser. Nos. 10/603,006 and 10/810,751, the contents of each of which are herein incorporated by reference).

The results of these studies showed that 37 percent of tissue samples positively stained for the 7BD-33-11A antigen. Expression of 7BD-33-11A within patient samples appeared specific for cancer cells as staining was restricted to malignant cells. In addition, 7BD-33-11A stained 0 of 20 samples of normal tissue from breast cancer patients. Breast tumor expression of the 7BD-33-11A antigen appeared to be localized to the cell membrane and cytoplasm of malignant cells, making CD63 an attractive target for therapy.

As disclosed in Ser. No. 10/810,751, the contents of which are herein incorporated by reference, 7BD-33-11A was compared to RFAC4 and H5C6 and to an anti-Her2 antibody (c-erbB-2). The results of the current study were similar to previous results and showed that 36 percent of tumor tissue samples stained positive for the 7BD-33-11A antigen while 94 and 85 percent of breast tumor tissues were positive for the H5C6 and RFAC4 epitope respectively. Expression of 7BD-33-11A within patient samples appeared specific for cancer cells as staining was restricted to malignant cells. In addition, 7BD-33-11A stained 0 of 10 samples of normal tissue from breast cancer patients while both H5C6 and RFAC4 stained 7 of 8 samples of normal breast tissue. In comparison to c-erbB-2, 7BD-33-11A showed a completely different staining profile where half of the breast tumor tissue samples that were positive for the 7BD-33-11A antigen were negative for Her2 expression indicating that 7BD-33-11A targets a patient population that is not served by existing antibody therapies. There were also differences in the intensity of staining between the breast tumor tissue sections that were positive for both 7BD-33-11A and Her2. The c-erbB-2 antibody also positively stained one of the normal breast tissue sections.

As disclosed in Ser. No. 10/603,006, Ser. No. 10/810,751 and Ser. No. 11/321,624, the contents of each of which are herein incorporated by reference, 7BD-33-11A expression was further evaluated based on breast tumor expression of the receptors for the hormones estrogen and progesterone, which play an important role in the development, treatment, and prognosis of breast tumors. There was a slight correlation between absence of estrogen receptors and presence of progesterone receptors and 7BD-33-11A antigen expression. When tumors were analyzed based on their stage, or degree to which the cancer advanced, results suggested a trend towards greater positive expression with higher tumor stage for 7BD-33-11A. Similar results were obtained with RFAC4. H5C6 also showed a very slight correlation with estrogen or progesterone receptor expression but there was no apparent correlation with tumor stage, however, conclusions were limited by the small sample size.

Localization of the 7BD-33-11A antigen and its prevalence within prostate cancer patients is important in assessing the benefits of 7BD-33-11A immunotherapy to patients with prostate cancer and designing effective clinical trials. To address 7BD-33-11A antigen expression in prostate tumors from cancer patients, tumor tissue samples from 51 individual prostate cancer patients were screened for expression of the 7BD-33-11A antigen (as disclosed in Ser. No. 10/810,751, the contents of which are herein incorporated by reference). The results of the study showed that 88 percent of tissue samples stained positive for the 7BD-33-11A antigen. Although 7BD-33-11A stained the normal tissue sections with high intensity as well, there was a higher degree of membranous staining in the tumor tissue samples in comparison to the normal samples. There was one embryonal rhabdomyosarcroma tissue sample that did not stain for the 7BD-33-11A antigen. In the small sample size tested there did not appear to be a direct correlation between tumor stage and presence of the 7BD-33-11A antigen.

Localization of the 7BD-33-11A antigen and its prevalence within melanoma cancer patients is important in assessing the benefits of 7BD-33-11A immunotherapy to patients with melanoma and designing effective clinical trials. To address 7BD-33-11A antigen expression in melanoma tumors from cancer patients, tumor tissue samples from 39 individual melanoma patients were screened for expression of the 7BD-33-11A antigen (as disclosed in Ser. No. 11/321,624). The results of the study showed that 90 percent of tissue samples stained positive for the 7BD-33-11A antigen. In this small sample, there also appeared to be no direct correlation between tumor stage and presence of the 7BD-33-11A antigen.

To further extend the potential therapeutic benefit of 7BD-33-11A, the frequency and localization of the antigen within various human cancer tissues was also determined (disclosed in Ser. Nos. 10/603,006, 10/810,751 and 11/321,624, the contents of each of which are herein incorporated by reference). Several cancer types, in addition to breast and prostate cancer, expressed the 7BD-33-11A antigen. The positive human cancer types included skin (1/2), lung (3/4), liver (2/3), stomach (4/5), thyroid (2/2), uterus (4/4) and kidney (3/3). Some cancers did not express the antigen; these included ovary (0/3), testis (0/1), brain (0/2) and lymph node (0/2). As with human breast, prostate and melanoma cancer tissue, localization of 7BD-33-11A occurred both on the membrane and within the cytoplasm of these tumor cells. Therefore, in addition to the 7BD-33-11A antibody binding to cancer cell lines in vitro, there is evidence that the antigen is expressed in humans, and on multiple types of cancers.

As disclosed in Ser. No. 10/810,751, the contents of which are herein incorporated by reference biochemical data also indicate that the antigen recognized by 7BD-33-11A is CD63. This is supported by studies showing that the monoclonal antibody RFAC4, reactive against CD63, identifies proteins that bound to 7BD-33-11A by immunoprecipitation. In addition, bacterial expression studies elucidated that 7BD-33-11A bound to extracellular loop 2 of CD63. The 7BD-33-11A epitope was also distinguished by being conformation dependent. These IHC and biochemical results demonstrate that 7BD-33-11A binds to the CD63 antigen. Thus, the preponderance of evidence shows that 7BD-33-11A mediates anti-cancer effects through ligation of unique conformational epitope(s) present on CD63. For the purpose of this invention, said epitope is defined as a "CD63 antigenic moiety" characterized by its ability to bind with a monoclonal antibody encoded by the hybridoma cell line 7BD-33-11A, antigenic binding fragments thereof or antibody conjugates thereof.

In toto, this data demonstrates that the 7BD-33-11A antigen is a cancer associated antigen and is expressed in humans, and is a pathologically relevant cancer target. Further, this data also demonstrates the binding of the 7BD-33-11A antibody to human cancer tissues, and can be used appropriately for assays that can be diagnostic, predictive of therapy, or prognostic. In addition, the cell membrane localization of this antigen is indicative of the cancer status of the cell due to the relative infrequency of expression of the antigen in most non-malignant cells, and this observation permits the use of this antigen, its gene or derivatives, its protein or its variants to be used for assays that can be diagnostic, predictive of therapy, or prognostic.

The present invention describes the development and use of 7BD-33-11A developed by the process described in patent U.S. Pat. No. 6,180,357 and identified by, its effect, in a cytotoxic assay, in tumor growth in animal models and in prolonging survival time in those suffering from cancerous disease.

This invention represents an advance in the field of cancer treatment in that it describes reagents that bind specifically to an epitope or epitopes present on the target molecule, CD63, and that also have in vitro anti-metastatic properties against malignant liver tumor cells but not normal cells, and which also directly mediate inhibition of tumor growth, metastasis and extension of survival in in vivo models of human liver cancer. The preponderance of evidence, disclosed herein, demonstrates that 7BD-33-11A mediates anti-cancer effects through ligation of epitopes present on CD63, which is expressed on liver cancer, which will broadly be understood to encompass any primary or metastatic tumor sites which arises from hepatocytes. This application demonstrates that for patients with liver cancer, CD63 expression is inversely correlated with overall patient survival. In addition, higher expression of CD63 is observed with metastatic versus primary human liver cancer tissue samples and cell lines. This invention also discloses that 7BD-33-11A decreases the growth, migration and invasion of $CD63^+$ human liver cancer cells in vitro and reduces the tumor burden and probability of metastasis of human liver cancer in vivo.

This is an advance in relation to any other previously described anti-CD63 antibody, since none have been shown to have similar properties. It also provides an advance in the field since it clearly demonstrates the direct involvement of CD63 in events associated with growth and development of certain types of tumors. It also represents an advance in cancer therapy since it has the potential to display similar anti-cancer properties in human patients. A further advance is that inclusion of these antibodies in a library of anti-cancer antibodies will enhance the possibility of targeting tumors expressing different antigen markers by determination of the appropriate combination of different anti-cancer antibodies, to find the most effective in targeting and inhibiting growth and development of the tumors.

In all, this invention teaches the use of the 7BD-33-11A antigen as a target for a therapeutic agent, that when administered can reduce the tumor burden and the likelihood of metastasis of a cancer expressing the antigen in a mammal, and can also lead to a prolonged survival of the treated mammal.

Accordingly, it is an objective of the invention to utilize a method for producing cancerous disease modifying antibodies (CDMAB) raised against cancerous cells derived from a particular individual, or one or more particular cancer cell lines, which CDMAB are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies, ligands, CDMAB and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies and CDMABs which are useful in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 is a summary of 7BD-33-11A binding on a human liver tumor and normal tissue microarray.

FIG. 2. Representative micrographs showing the binding pattern on liver tumor tissue obtained with 7BD-33-11A on hepatocellular carinoma (A) or the isotype control antibody on hepatocellular carinoma (C) or with 7BD-33-11A on metastatic cholangiocarcinoma (B) or the isotype control antibody on metastatic cholangiocarcinoma (D) from a human tissue microarray. 7BD-33-11A displayed strong positive staining for the tumor cells. Magnification is 200×.

FIG. 3 demonstrates the correlation between CD63 and HCC metastasis on a tissue microarray containing 60 pairs of primary HCC and their matched metastatic tumors.

FIG. 4. CD63 expression in hepatocellular carcinoma (HCC) tissue microarray.

FIG. 6. Correlation of CD63 over-expression and clinicopathical features of HCC patients FIG. 7 demonstrates correlation between CD63 overexpression and metastatic potential of various HCC cell lines.

FIG. 8 demonstrates the in vitro functional role of CD63 in the Hep3B HCC cell line.

FIG. 9 demonstrates the in vitro effect of 7-BD-33-11A on the MHCC-97H HCC cell line.

FIG. 10 demonstrates the effect of 7BD-33-11A on HCC tumor growth in an established orthotopic HCC tumor model. Data points represent the mean+/−SEM.

FIG. 12 demonstrates the effect of 7BD-33-11A on HCC metastasis in an established metastatic HCC tumor model. Data points represent the mean+/−SEM.

DETAILED DESCRIPTION OF THE INVENTION

Figure 5:
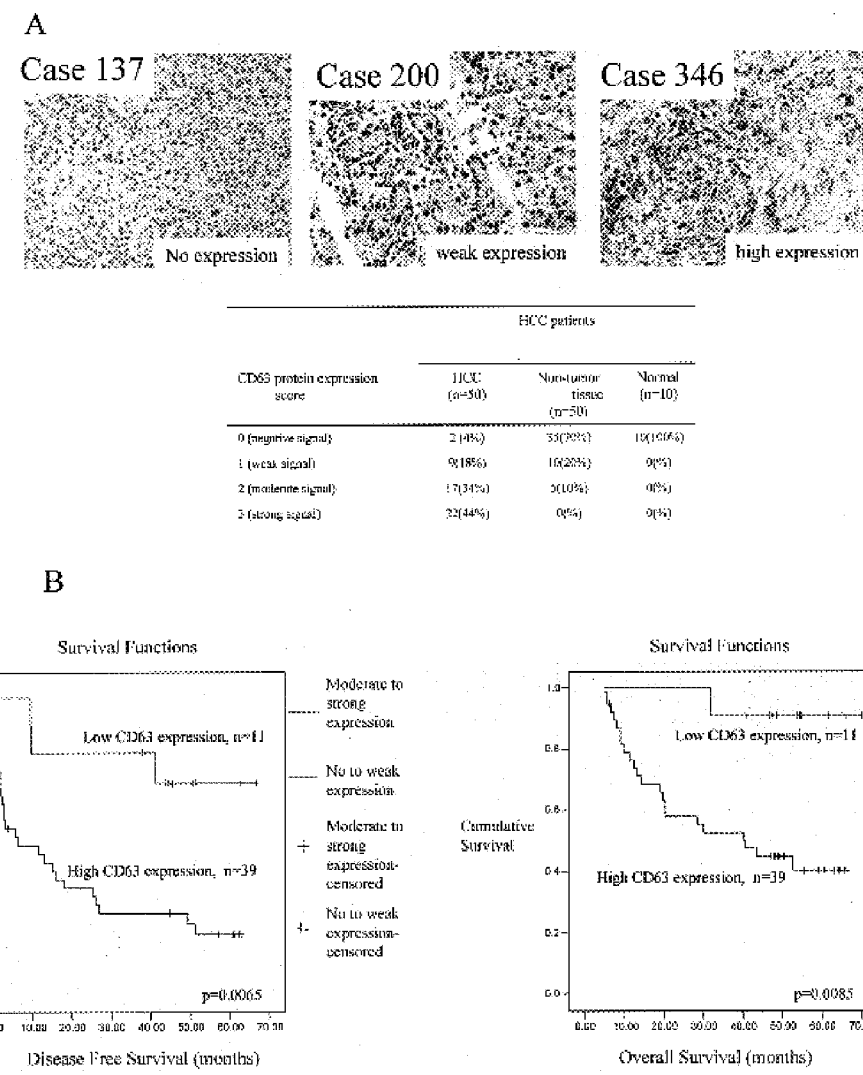
FIG. 5 demonstrates the clinical significance of CD63 over-expression in HCC.

In general, the following words or phrases have the indicated definition when used in the summary, description, examples, and claims.

The term "antibody" is used in the broadest sense and specifically covers, for example, single monoclonal antibodies (including agonist, antagonist, and neutralizing antibodies, de-immunized, murine, chimerized or humanized antibodies), antibody compositions with polyepitopic specificity, single chain antibodies, immunoconjugates and fragments of antibodies (see below).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

"Antibody fragments" comprise a portion of an intact antibody, preferably comprising the antigen-binding or variable region thereof. Examples of antibody fragments include less than full length antibodies, Fab, Fab', F(ab')$_2$, and Fv fragments; diabodies; linear antibodies; single-chain antibody molecules; single-chain antibodies, single domain antibody molecules, fusion proteins, recombinant proteins and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called a, d, e, ?, and µ, respectively. The subunit structures and three-dimensional configurations of different classes of immunoglobulins are well known.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express Fc?RIII only, whereas monocytes express Fc?RI, Fc?RII and Fc?RIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998).

"Effector cells" are leukocytes which express one or more FcRs and perform effector functions. Preferably, the cells express at least Fc?RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fe region of an antibody. The preferred FcR is a native sequence human FcR. Moreover, a preferred FcR is one which binds an IgG antibody (a gamma receptor) and includes receptors of the Fc?RI, Fc?RII, and Fc? RIII subclasses, including allelic variants and alternatively spliced forms of these receptors. Fc?RII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, Annu. Rev. Immunol 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., Eur. *J. Immunol.* 24:2429 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the >sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 2632 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (?) and lambda (?), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies,* vol. 113, Rosenburg and Moore eds., Springer-Verlag, New York, pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other protcinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An antibody "which binds" an antigen of interest, e.g. CD63 antigenic moiety, is one capable of binding that antigen with sufficient affinity such that the antibody is useful as a therapeutic or diagnostic agent in targeting a cell expressing the antigen. Where the antibody is one which binds CD63 antigenic moiety it will usually preferentially bind CD63 antigenic moiety as opposed to other receptors, and does not include incidental binding such as non-specific Fc contact, or binding to post-translational modifications common to other antigens and may be one which does not significantly cross-react with other proteins. Methods, for the detection of an antibody that binds an antigen of interest, are well known in the art and can include but are not limited to assays such as FACS, cell ELISA and Western blot.

As used herein, the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Hence, the mammal to be treated herein may have been diagnosed as having the disorder or may be predisposed or susceptible to the disorder.

The terms "cancer" and "cancerous" refer to or describe the physiological condition in mammals that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2?-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

"Mammal" for purposes of treatment refers to any animal classified as a mammal, including humans, mice, SCID or nude mice or strains of mice, domestic and farm animals, and zoo, sports, or pet animals, such as sheep, dogs, horses, cats, cows, etc. Preferably, the mammal herein is human.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., *Nucl. Acids Res.,* 14:5399-5407, 1986. They are then purified on polyacrylamide gels.

Unless indicated otherwise, the term "CD63 antigenic moiety" when used herein refers to the Type III membrane protein of the tetraspanin family also referred to as melanoma 1 antigen, ocular melanoma-associated antigen, melanoma associated antigen ME491, lysosome-associated membrane glycoprotein 3, granulophysin, melanoma-associated antigen MLA1.

"Chimeric" antibodies are immunoglobulins in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 and Morrison et al, *Proc. Natl. Acad. Sci. USA*, 81:6851-6855 (1984)).

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

"De-immunized" antibodies are immunoglobulins that are non-immunogenic, or less immunogenic, to a given species. De-immunization can be achieved through structural alterations to the antibody. Any de-immunization technique known to those skilled in the art can be employed. One suitable technique for de-immunizing antibodies is described, for example, in WO 00/34317 published Jun. 15, 2000.

"Homology" is defined as the percentage of residues in the amino acid sequence variant that are identical after aligning the sequences and introducing gaps, if necessary, to achieve the maximum percent homology. Methods and computer programs for the alignment are well known in the art.

Throughout the instant specification, hybridoma cell lines, as well as the isolated monoclonal antibodies which are produced therefrom, are alternatively referred to by their internal designation, 7BD-33-11A, or Depository Designation, ATCC PTA-4890, As used herein "antibody-ligand" includes a moiety which exhibits binding specificity for a target antigen, and which may be an intact antibody molecule, antibody fragments, and any molecule having at least an antigen-binding region or portion thereof (i.e., the variable portion of an antibody molecule), e.g., an Fv molecule, Fab molecule, Fab' molecule, F(ab').sub.2 molecule, a bispecific antibody, a fusion protein, or any genetically engineered molecule which specifically recognizes and binds the antigen bound by the isolated monoclonal antibody produced by the hybridoma cell line designated as ATCC PTA-4890 (the ATCC PTA-4890 antigen).

As used herein "cancerous disease modifying antibodies" (CDMAB) refers to monoclonal antibodies which modify the cancerous disease process in a manner which is beneficial to the patient, for example by reducing tumor burden or prolonging survival of tumor bearing individuals, and their antibody-ligands thereof.

As used herein "antigen-binding region" means a portion of the molecule which recognizes the target antigen.

As used herein "competitively inhibits" means being able to recognize and bind a determinant site to which the monoclonal antibody produced by the hybridoma cell line designated as ATCC PTA-4890 (ATCC PTA-4890 antibody) is directed using conventional reciprocal antibody competition assays. (Belanger L., Sylvestre C. and Dufour D. (1973), Enzyme linked immunoassay for alpha fetoprotein by competitive and sandwich procedures. Clinica Chimica Acta 48, 15).

As used herein "target antigen" is the ATCC PTA-4890 antigen or portions thereof.

As used herein, an "immunoconjugate" means any molecule or antibody-ligand such as an antibody chemically or biologically linked to a cytotoxin, a radioactive agent, enzyme, toxin, an anti-tumor drug or a therapeutic agent. The antibody or CDMAB may be linked to the cytotoxin, radioactive agent, anti-tumor drug or therapeutic agent at any location along the molecule so long as it is able to bind its target. Examples of immunoconjugates include antibody toxin chemical conjugates and antibody-toxin fusion proteins.

As used herein, a "fusion protein" means any chimeric protein wherein an antigen binding region is connected to a biologically active molecule, e.g., toxin, enzyme, or protein drug.

In order that the invention herein described may be more fully understood, the following description is set forth.

The present invention provides CDMABs (i.e., ATCC PTA-4890 CDMABs) which specifically recognize and bind the ATCC PTA-4890 antigen.

The CDMAB of the isolated monoclonal antibody produced by the hybridoma deposited with the ATCC as accession number PTA-4890 may be in any form as long as it has an antigen-binding region which competitively inhibits the immunospecific binding of the isolated monoclonal antibody produced by hybridoma ATCC PTA-4890 to its target antigen. Thus, any recombinant proteins (e.g., fusion proteins wherein the antibody is combined with a second protein such as a lymphokine or a tumor inhibitory growth factor) having the same binding specificity as the ATCC PTA-4890 antibody fall within the scope of this invention.

In one embodiment of the invention, the CDMAB is the ATCC PTA-4890 antibody.

In other embodiments, the CDMAB is an antigen binding fragment which may be a Fv molecule (such as a single chain Fv molecule), a Fab molecule, a Fab' molecule, a F(ab')2 molecule, a fusion protein, a bispecific antibody, a heteroantibody or any recombinant molecule having the antigen-binding region of the ATCC PTA-4890 antibody. The CDMAB of the invention is directed to the epitope to which the ATCC PTA-4890 monoclonal antibody is directed.

The CDMAB of the invention may be modified, i.e., by amino acid modifications within the molecule, so as to produce derivative molecules. Chemical modification may also be possible.

Derivative molecules would retain the functional property of the polypeptide, namely, the molecule having such substitutions will still permit the binding of the polypeptide to the ATCC PTA-4890 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Given an antibody, an individual ordinarily skilled in the art can generate a competitively inhibiting CDMAB, for example a competing antibody, which is one that recognizes the same epitope (Belanger et al., 1973). One method could entail immunizing with an immunogen that expresses the antigen recognized by the antibody. The sample may include but is not limited to tissue, isolated protein(s) or cell line(s). Resulting hybridomas could be screened using a competing assay, which is one that identifies antibodies that inhibit the binding of the test antibody, such as ELISA, FACS or immunoprecipiation. Another method could make use of phage display libraries and panning for antibodies that recognize said antigen (Rubinstein et al., 2003). In either case, hybridomas would be selected based on their ability to out-compete the binding of the original antibody to its target antigen. Such hybridomas would therefore possess the characteristic of recognizing the same antigen as the original antibody and more specifically would recognize the same epitope.

EXAMPLE 1

Human Liver Tumor Tissue Staining

IHC studies were conducted to evaluate the binding of 7BD-33-11A to human liver tumor tissue. IHC optimization studies were performed previously in order to determine the conditions for further experiments.

Tissue sections were deparaffinized by drying in an oven at 58° C. for 1 hour and dewaxed by immersing in xylene 5 times for 4 minutes each. Following treatment through a series of graded ethanol washes (100 percent-75 percent) the sections were re-hydrated in water. The slides were immersed in 10 mM citrate buffer at pH 6 (Dako, Toronto, Ontario) then microwaved at high, medium, and low power settings for 5 minutes each, then left 15 minutes at room temperature and washed with PBS 3 times for minutes each. Slides were then immersed in 3 percent hydrogen peroxide solution for 10 minutes, washed with PBS three times for 5 minutes each, then incubated with Universal blocking solution (Dako, Toronto, Ontario) for 5 minutes at room temperature. 7BD-33-11A, monoclonal mouse anti-alpha Fetoprotein (Abcam, Cambridge, Mass.) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 micrograms/mL) for each antibody except for anti-Alpha feto protein which was diluted according to data sheet recommendation (10 micrograms/mL) and incubated for 1 hour at room temperature. The slides were washed with PBS 3 times for 5 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehydrated with graded ethanols (75-100 percent) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a histopathologist.

Binding of the antibodies to 49 human liver tumor (45 hepatocellular carcinoma and 4 cholangiocarcinoma) and 9 non-neoplastic liver tissues was performed using a human liver, normal and tumor, tissue microarray (Imgenex, San Diego, Calif.). FIG. 1 presents a summary of the results of 7BD-33-11A staining of an array of human non-neoplastic and tumor liver tissues. Each non-neoplastic or tumor sample is represented by one spot. As shown in FIG. 1, 7BD-33-11A bound to $39/49$ (80 percent) sections on the human liver tumor tissue microarray. The antibody showed strong (+++) staining in $3/49$ sections, moderate (++) staining in $15/49$ sections, weak (+) staining in $18/49$ sections and equivocal (+/−) staining in $3/49$ sections. The binding was restricted to tumor cells and infiltrating inflammatory cells in some tumors. The cellular localization was cytoplasmic and membranous with a granular staining pattern. Heterogeneous binding was observed to the tumor cells, ranging between <10 percent to >50 percent. According to the histological type of the liver tumors available on the tissue microarray, there was binding to $36/45$ (80 percent) of the hepatocellular carcinomas and to $3/4$ (75 percent) of the cholangiocarcinomas. 7BD-33-11A showed a binding preference to metastatic liver tumors. There was binding to $7/8$ (88 percent) of the metastatic hepatocellular carcinomas compared to $29/37$ (78 percent) of the primary hepatocellular carcinomas, and to $2/2$ (100 percent) of the metastatic cholangiocarcinomas compared to $1/2$ (50 percent) of the primary cholangiocarcinomas. There was binding to $9/9$ (100 percent) of the non-neoplastic liver tissues; binding was to hepatocytes. The cellular localization was cytoplasmic and membranous with a granular staining pattern (FIG. 2).

In relation to tumor differentiation of primary hepatocellular carcinomas, 7BD-33-11A showed a trend towards higher binding to poorly differentiated tumors, as there was binding to $4/4$ (100 percent), $16/19$ (84 percent) and $4/5$ (80 percent) of poorly, moderately and well differentiated primary hepatocellular carcinomas, respectively.

In relation to AJCC stages of liver cancers, there was binding of the antibody to $1/2$ (50 percent), $15/17$ (88 percent), $12/16$ (75 percent) and $5/8$ (63 percent) of the sections from stages I, II, III and IV respectively. Therefore, no relation could be found between the antibody binding and TNM stages. This lack of correlation may be due to the small sample size for some of the cancer stages.

Therefore, the 7BD-33-11A antigen appears to be expressed on liver tumor tissue with some binding preference for metastatic liver tumor tissue. There also was a trend of higher binding to less differentiated primary hepatocellular carcinomas. 7BD-33-11A therefore has utility as a diagnostic reagent for hepatocellular carcinoma, and as a therapeutic drug in the treatment of liver cancer.

EXAMPLE 2

Immunostaining on Hepatocellular Carcinoma Tissue Microarray

To further study the results obtained in Example 1, 7BD-33-11A binding was directly compared to human primary and mestastatic hepatocellular carcinoma tissue. With reference to FIG. 3, the human hepatocellular carcinoma (HCC) tissue microarray was constructed as outlined below. Briefly, tissue samples were obtained from Eastern Hepato-biliary Surgery Hospital (Shanghai, China) from 1995 to 1999 and were embedded in paraffin using standard protocols. The embedded tissue samples were freshly sectioned and stained with hematoxylin and eosin. The representative regions of lesion were reviewed carefully and defined by two pathologists. Based on the clinicopathological information, specimens were grouped in tissue cylinders and a diameter of 0.6 mm was taken from the selected regions of the donor block and then punched precisely into a recipient paraffin block using a tissue array instrument (Beecher Instruments, Silver Spring, Md.). Consecutive 5 micrometer sections of the microarray blocks were made with a microtome. Finally, a TMA section with 60 pairs of primary and matched metastatic HCC samples (including 31 intrahepatic and 29 extrahepatic metastases) was constructed.

To determine a possible role of CD63 in HCC metastasis, CD63 expression was evaluated on the HCC tissue microarray by immunostaining with the 7BD-33-11A antibody. An overview of the tissue array section containing 60 pairs of primary HCC and their matched metastatic tumors showing Twist expression is shown in FIG. 3A. In 60 pairs of primary HCC and their corresponding metastatic tumors, high cytoplasmic CD63 expression could be detected in $26/54$ (48 percent) and $43/57$ (75 percent) of the primary and metastatic HCC, respectively (FIG. 3B). Although 60 cases of primary and their matched metastatic HCCs were dotted in the tissue microarray, informative cases were found for 54 and 57 of the cases for primary and metastatic HCCs respectively. CD63 expression was significantly associated with HCC metastasis ($p<0.001$). CD63 protein expression in primary and corresponding metastatic HCC is summarized in FIG. 4. 7BD-33-11A therefore has utility in the diagnosis of HCC.

EXAMPLE 3

Immunostaining on 50 Cases of Paraffin-Embedded HCC Tumor Tissues

To determine the correlation of CD63 expression with several clinical pathological features, immunostaining was performed on 50 cases of paraffin-embedded human HCC clinical samples, obtained during 1999 to 2001 from the Department of Surgery, University of Hong Kong Medical Centre, Queen Mary Hospital, Hong Kong, with the 7BD-33-11A antibody (FIG. 5).

Cytoplasmic expression of CD63 was determined by two independent observers who visually assessed the percentage of stained tumor cells as well as staining intensity. The percentage of positive cells was rated as follows: 2 points, 11-50 percent positive tumor cells; 3 points, 51-80 percent positive cells; and 4 points, >81 percent positive cells. Staining intensity was rated as follows: 1 point, weak intensity; 2 points, moderate intensity; and 3 points, strong intensity. Points for expression and percentage of positive cells were added, and specimens were attributed to four groups according to their overall scores: negative, $\leq 10$ percent of cells stained positive, regardless of intensity; weak expression, 3 points; moderate expression, 4-5 points; and strong expression, 6-7 points. Negative to weak CD63 expression was graded as group 1, which represented low CD63 expression; whereas moderate to strong CD63 expression was graded as group 2, which represented high CD63 expression.

There was no cytoplasmic staining in the liver of normal healthy donors. In non-tumor tissues (non-cirrhotic and cirrhotic), CD63 expression was detected in $15/50$ (30 percent) samples. The 30 percent binding of 7BD-33-11A to non-neoplastic liver sections is lower than that found in Example 1. This could be attributed to differences in tissue sampling, the staining methodology or scoring system.

In HCC, 48 out of 50 cases (96 percent) showed positive cytoplasmic staining in HCC (FIG. 3A). The correlation between CD63 expression with clinical pathological features was summarized in FIG. 6. The 39 cases with high CD63 expression were significantly associated with recurrence of cancer during the first year ($p=0.001$), advanced tumor stages ($p=0.014$), and venous infiltration ($p=0.001$). The disease-free survival (DFS) and overall survival (OS) was then analyzed by comparing the HCC patients with low or high CD63 expression in tumor cells. Assessed by Kaplan-Meier analysis (FIG. 5B), patients with high CD63 expression had a shorter DFS than patients who had no or low CD63 expression ($p=0.0065$). Also, patients who demonstrated high CD63 expression consistently had a shorter OS than those with low CD63 expression ($p=0.0085$).

Therefore, the data demonstrate that CD63 expression is correlated with a greater likelihood of cancer recurrence, advanced tumor stage, venous infiltration and poorer disease-free and overall survival. Consequently, 7BD-33-11A has utility in determination of correlation with a greater likelihood of cancer recurrence, advanced tumor stage, venous infiltration and poorer disease-free and overall survival associated with HCC.

EXAMPLE 4

Correlation of CD63 with Metastatic Potential of Various HCC Cell Lines

In Examples 2 and 3, it was demonstrated that there is a correlation between CD63 expression and HCC metastasis in clinical samples. To further evaluate this correlation in vitro, six HCC cell lines, HepG2 and Hep3B (American Type Culture Collection, Manassas, Va.), Huh-7 (a gift from Dr. H. Nakabayashi, Hokkaido University School of Medicine, Sapporo, Japan), PLC (Japanese Cancer Research Bank, Tokyo, Japan), MHCC-97L and MHCC-97H (Liver Cancer Institute, Fudan University, Shanghai, China), with various metastatic potential were evaluated for CD63 expression by flow cytometry using 7BD-33-11A. To detect expression of CD63 in various HCC cell lines, cells were stained for 1 hour with 7BD-33-11A (10 microgramsg/mL) or isotype control (IgG2a, clone eBM2a, eBioscience, San Diego, Calif.; 10 microgramsg/mL) followed by 30 minutes incubation with 1 microgram of goat anti-mouse FITC-conjugated secondary antibody (eBioscience, San Diego, Calif.). The samples were then analyzed by FACS.

Figure 7:
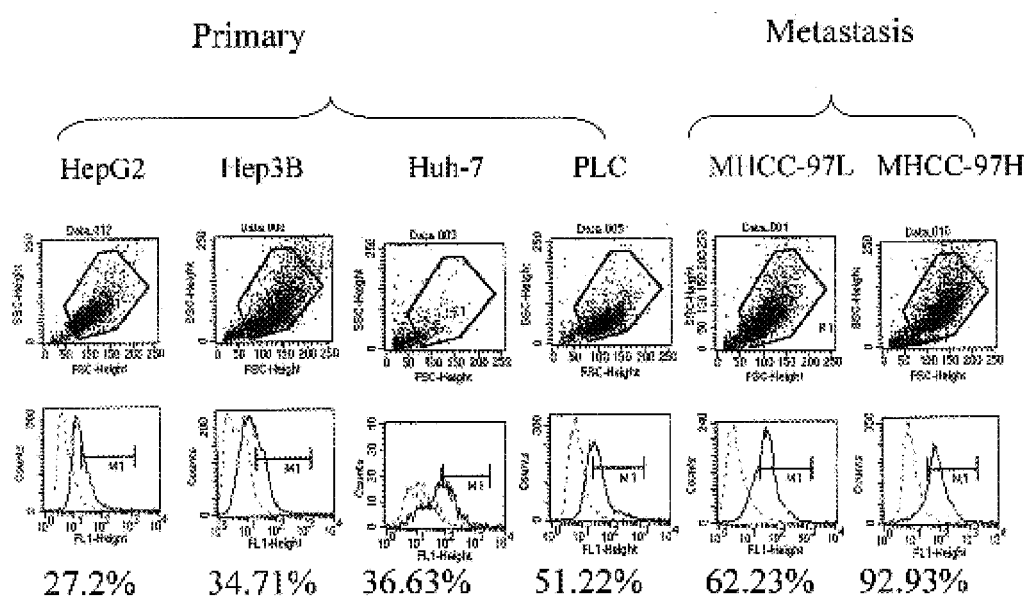

By flow cytometry, CD63 protein levels were found to be higher in the metastatic HCC cell lines (MHCC-97L and MHCC-97H) when compared with the primary non-metastatic cell lines (HepG2, Hep3B, Huh-7 and PLC) (FIG. 7).

This demonstrates that CD63 over-expression is associated with advanced HCC and consequently, 7BD-33-11A can be used for this determination. This evidence is consistent with Examples 2 and 3.

EXAMPLE 5

Functional Analysis of CD63 in HCC by Cell Sorting

With reference to FIG. 8, the functional role of CD63 over-expression in a HCC cell line was examined by cell sorting. Hep3B cells were first labeled with 1 microgram of anti-CD63 (MX-49.129.5, Santa Cruz Biotechnology, Santa Cruz, Calif.) antibody for an hour. CD63 positive cells were sorted by a FACSCalibur machine (BD Biosciences, San Jose, Calif.). CD63$^+$ and CD63$^-$ cells were sorted into DMEM medium with 10 percent FBS. A proliferation assay, wound healing assay and invasion assay were performed to evaluate the proliferation, motility and invasion of the sorted cells.

For the proliferation assay, the cells were plated in a six well plate at 1000 cells/well. The growth of the colonies was examined 2 weeks later with Giema stain. Cell migration was assessed by measuring the movement of cells into a scraped, acellular area created by a 200 microliter pipette tube (time 0) and the speed of wound closure was monitored after 24 hours. Invasion assays were performed with 24-well BioCoat Matrigel Invasion Chambers (Becton, Dickinson and Company, Franklin Lakes, N.J.) using $5\times10^4$ cells in serum-free DME and plated onto either control or matrigel-coated filters. Conditioned medium from PLC or PLC-Twist cells was placed in the lower chambers as chemoattractants. After 22 hours in culture, the cells were removed from the upper surface of the filter by scraping with a cotton swab. The cells that invaded through the matrigel and were adherent to the bottom of the membrane were stained with crystal violet solution. The cell-associated dye was eluted with 10 percent acetic acid and its OD at 595 nm was determined. Each experiment was done in triplicate and the mean values±SEM were presented.

After cell sorting, the purity of the two populations of Hep3B cells was determined by flow cytometry. The CD63$^+$ population of cells was 92 percent pure while purity of the CD63$^-$ population of cells was 86 percent (FIG. 8A). The colony formation assay showed that CD63$^+$ cells have a faster rate of cell proliferation when compared with CD63$^-$ cells (FIG. 8B). The HCC cell invasiveness as evaluated by the invasion assay demonstrated that CD63$^+$ cells showed an increased invasion when compared with CD63$^-$ cells (FIG. 8C). The wound healing assay, also shown in FIG. 8D, demonstrated that the migration rate of CD63$^+$ Hep3B cells was faster than CD63$^-$ Hep3B cells. Arrows indicate differential migration rates between the two cell populations. In summary, these results demonstrate that CD63 expression on HCC cells correlates with cell proliferation, increased invasion and higher migration and that 7BD-33-11A is useful for such detection.

EXAMPLE 6

In-Vitro Efficacy of 7BD-33-11A on Growth, Motility and Invasion of Human MHCC-97H HCC Cells To further the results obtained in Example 5 with the Hep3B cell line, 7BD-33-11A was added to MHCC-97H cells at doses of 2, 10 and 20 micrograms/mL for two weeks for the colony formation assay and 48 hours for the wound healing and invasion assay (FIG. 9). Colony formation, cell motility and invasion assays were employed as described above, to evaluate the effect of 7BD-33-11A on proliferation, cell motility and invasion of human MHCC-97H HCC cells. 7BD-33-11A suppressed MHCC-97H growth in a dose-dependent manner (FIG. 9A). In addition, 7BD-33-11A significantly suppressed MHCC-97H cell motility and invasion as evidenced by the wound healing and invasion assay respectively (FIGS. 9B and 9C respectively). These results support the conclusions from Example 5 and further demonstrate the direct utility of 7BD-33-11A in reducing the growth, migration and invasion of human metastatic HCC cells.

EXAMPLE 7

Orthotopic HCC Tumor Model with MHCC-97H Cells

Figure 11:
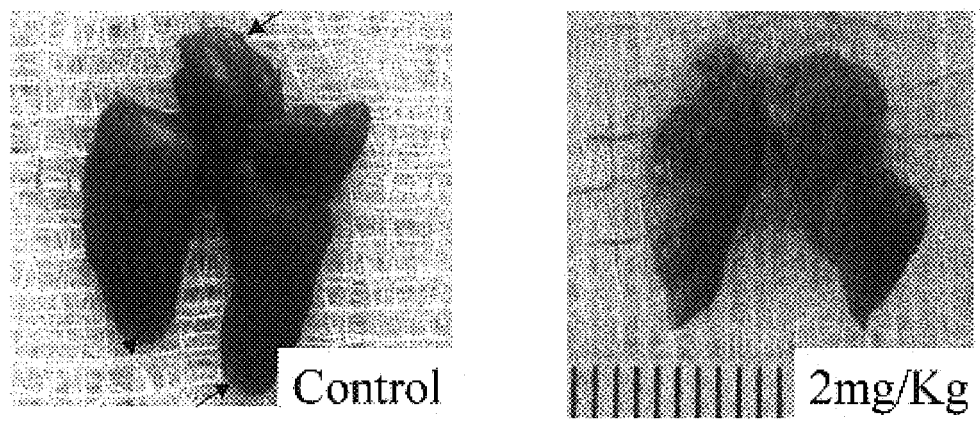
FIG. 11 demonstrates the effect of 7BD-33-11A on intrahepatic and lung metastasis in an established orthotopic HCC tumor model. Data points represent the mean +/−SEM.

To determine the effect of 7BD-33-11A on human metastatic liver cells in vivo, approximately $1\times10^7$ human metastatic HCC MHCC-97H cells in 0.2 mL of culture medium was injected subcutaneously (s.c.) into the right flank of 5-week-old male nude mice (obtained from Lab Animal Unit at the University of Hong Kong, Hong Kong), which were then observed daily for signs of tumor development (FIGS. 10 and 11). Once the tumor reached a size of 1 to 1.5 cm in diameter, it was removed and cut into about 1- to 2-mm cubes, which were implanted into the left liver lobe of 5 week old male nude mice, using a previously described method (Lee et al., 2005). Ten days later, the nude mice were randomized into six groups of five and were treated with 2, 5 or 10 mg/kg of either isotype control (IgG2a, clone eBM2a, eBioscience, San Diego, Calif.), or 7BD-33-11A. 7BD-33-11A test antibody was administered intraperitoneally to each cohort, in a volume of 200 microlitres after dilution from the stock concentration with a diluent that contained 2.7 mM KCl, 1 mM KH2PO$_4$, 137 mM NaCl and 20 mM Na$_2$HPO$_4$. The antibodies were then administered 2 times per week for a total of 12 doses in the same fashion until day 50 post-implantation. Body weights of the animals were recorded once per week for the duration of the study. At day 50, all animals were euthanised according to the guidelines from the Committee on the Use of Live Animals in Teaching and Research of the University of Hong Kong. Tumor growth was calculated using the equation length×width$^2$×0.5.

7BD-33-11A significantly reduced tumor burden in an established model of human HCC. On day 50 after tumor implantation, 7BD-33-11A decreased primary liver tumor volume, compared to isotype control, from 1,559±252 to 854±86, 346.5±24 mm$^3$ and 65±3.4 mm$^3$ at the doses of 2, 10 and 20 mg/kg, respectively. (p=0.0012, FIGS. 10A and 10B). Arrows in FIG. 10A indicate intrahepatic metastasis. Body weight measured at weekly intervals was used as a surrogate for well-being and failure to thrive. There was no significant difference in mean body weight between the two groups over the course of the study.

In addition, 7BD-33-11A significantly suppressed intrahepatic and lung metastases in an established orthotopic model of human HCC. The number of mice with lung and intrahepatic metastases in the treatment group and isotype control group are shown in FIG. 11B. Arrows in FIG. 11A indicate lung metastasis. 7BD-33-11A significantly suppressed intrahepatic metastasis from 4/5 (80 percent) to 1/5 (20 percent) at a dose of 2 mg/kg. 7BD-33-11A also significantly suppressed lung metastasis from 5/5 (100 percent) to 1/5 (20 percent) at the 2 mg/kg dose. All of the mice in the isotype control group showed no kidney or spleen metastasis.

In summary, 7BD-33-11A was well-tolerated, decreased the tumor burden and the probability of intrahepatic and lung metastases in this established human orthotopic HCC tumor model.

EXAMPLE 8

Metastatic HCC Tumor Model with MHCC-97H Cells

The effect of 7BD-33-11A on lung and intrahepatic metastases in the above model might be the result of an indirect effect; the reduction of the primary tumor results in a lower probably of metastases. To further evaluate the anti-metastatic efficacy of 7BD-33-11A on HCC and to determine whether it has a direct effect on the occurrence of metastases, a metastatic HCC tumor model was employed. With reference to FIG. 12, approximately $2\times10^6$ human metastatic MHCC-97H cells in 0.1 mL of culture medium was injected intravenously into 5-week-old male nude mice (obtained from the Lab Animal Unit at the University of Hong Kong, Hong Kong) through tail vein injections. One day later, the nude mice were randomized into groups of five and were treated either with isotype control (concentration, what antibody, from where) or 5 or 10 mg/kg 7BD-33-11A. 7BD-33-11A test antibody was administered intraperitoneally to each cohort, in a volume of 200 microlitres after dilution from the stock concentration with a diluent that contained 2.7 mM KCl, 1 mM $KH_2PO_4$, 137 mM NaCl and 20 mM $Na_2HPO_4$. The antibodies were then administered 2 times per week for a total of 12 doses in the same fashion for 2 months. After two months, the animals were sacrificed and autopsied and examined for tumor formation in both the lung and liver of nude mice.

7BD-33-11A significantly ($p<0.001$) suppressed liver and lung metastases in an established metastatic HCC tumor model. 7BD-33-11A significantly suppressed liver metastasis from 5/5 (100 percent) to 1/5 (20 percent) and 0/5 (0 percent) at the dose of 5 and 10 mg/kg, respectively (FIGS. 12A and 12C). 7BD-33-11A significantly suppressed lung metastasis from 5/5 (100 percent) to 0/5 (0 percent) and 0/5 (0 percent) at the doses of 5 and 10 mg/kg, respectively (FIGS. 12B and 12C).

In summary, 7BD-33-11A was well-tolerated and decreased the probability of intrahepatic and lung metastases in this established human orthotopic HCC tumor model. This further supports the data from Example 7 and demonstrates that 7BD-33-11A treatment prevents initiation of tumors at secondary sites in addition to reducing the tumor size of primary tumors.

The preponderance of evidence shows that 7BD-33-11A mediates anti-cancer effects through ligation of epitopes present on CD63, which is expressed on liver cancer. It has been shown that for patients with liver cancer, CD63 expression is inversely correlated with overall patient survival. In addition, higher expression of CD63 is observed with metastatic versus primary human liver cancer tissue samples and cell lines. It has also been shown that 7BD-33-11A decreases the growth, migration and invasion of CD63$^+$ human liver cancer cells in vitro and reduces the tumor burden and probability of metastasis of human liver cancer in vivo. Therefore, 7BD-33-11A has therapeutic potential for the diagnosis and treatment of liver cancer, broadly understood to include any primary or metastatic tumor sites which arise from hepatocytes.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of treating primary human liver tumor sites and metastatic liver tumor sites in a mammal, wherein said primary human liver tumor or metastatic liver tumor expresses at least one epitope of a CD63 antigen which specifically binds to the isolated monoclonal antibody produced by a hybridoma cell line deposited with the ATCC as accession number PTA-4890, comprising administration to said mammal of a tumor reducing effective amount of said isolated monoclonal antibody or an antigen binding fragment thereof, which antigen binding fragment competitively inhibits binding of said isolated monoclonal antibody to said isolated monoclonal antibody's target CD63 antigen, wherein said administration results in a reduction of said mammal's tumor burden.

2. The method of claim 1 wherein said isolated monoclonal antibody or antigen binding fragment thereof is conjugated to a cytotoxic moiety.

3. The method of claim 2 wherein said cytotoxic moiety is a radioactive isotope.

4. The method of claim 1 wherein said isolated monoclonal antibody or antigen binding fragment thereof activates complement or mediates antibody dependent cellular cytotoxicity.

5. The method of claim 1 wherein said isolated monoclonal antibody or antigen binding fragment thereof is humanized.

6. The method of claim 1 wherein said isolated monoclonal antibody or antigen binding fragment thereof is chimeric.

7. A method of treating primary human liver tumor sites and liver tumor metastatic sites susceptible to antibody induced cellular cytotoxicity in a mammal, wherein said primary human liver tumor or liver tumor metastasis expresses at least one epitope of a CD63 antigen which specifically binds to the isolated monoclonal antibody produced by a hybridoma cell line deposited with the ATCC as accession number PTA-4890, comprising administration to said mammal of a tumor reducing effective amount of said isolated monoclonal antibody or an antigen binding fragment thereof, which antigen binding fragment competitively inhibits binding of said isolated monoclonal antibody to the CD63 target antigen of said isolated monoclonal antibody, wherein said administration results in a reduction of said mammal's tumor burden.

8. The method of claim 7 wherein said isolated monoclonal antibody or antigen binding fragment thereof is conjugated to a cytotoxic moiety.

9. The method of claim 8 wherein said cytotoxic moiety is a radioactive isotope.

10. The method of claim 7 wherein said isolated monoclonal antibody or antigen binding fragment thereof activates complement or mediates antibody dependent cellular cytotoxicity.

11. The method of claim 7 wherein said isolated monoclonal antibody or antigen binding fragment thereof is humanized.

12. The method of claim 7 wherein said isolated monoclonal antibody or antigen binding fragment thereof is chimeric.

13. A process for treating human cancerous liver tumors which express an epitope or epitopes of human CD63 antigen which specifically binds the isolated monoclonal antibody produced by hybridoma cell line 7BD-33-11A having ATCC Accession No. PTA-4890, comprising:

administering to an individual suffering from said human cancerous liver tumor the isolated monoclonal antibody produced by the hybridoma cell line deposited with ATCC as accession number PTA-4890 or an antigen binding fragment thereof, which antigen binding fragment competitively inhibits binding of said isolated monoclonal antibody to the target CD63 antigen of said isolated monoclonal antibody, wherein said antigen binding fragment recognizes the same epitope or epitopes of CD63 as those recognized by the isolated monoclonal antibody produced by hybridoma cell line 7BD-33-11A having ATCC Accession No. PTA-4890; wherein binding of said epitope or epitopes results in a reduction in tumor burden.

14. The process of claim 1, wherein said primary human tumor sites and/or metastatic sites arise from hepatocytes.

15. The process of claim 8, wherein said primary human tumor sites and/or metastatic sites arise from hepatocytes.

16. The process of claim 15, wherein said human cancerous liver tumor arises from hepatocytes.

* * * * *

UNITED STATES PATENT AND TRADEMARK OFFICE
CERTIFICATE OF CORRECTION

PATENT NO. : 7,534,429 B2  
APPLICATION NO. : 11/493407  
DATED : May 19, 2009  
INVENTOR(S) : David S. F. Young et al.

Page 1 of 1

It is certified that error appears in the above-identified patent and that said Letters Patent is hereby corrected as shown below:

On the Title Page, Item -56- ("Other Publications"), line 1, delete "Jain" and insert -- Jain et al. --;

Column 40, line 1, claim 13, after "with" insert -- the --;

Column 41, line 12, claim 13, delete "in" and insert -- of --;

Column 40, line 15, claim 15, delete "claim 8," and insert -- claim 7, --;

Column 40, line 17, claim 16, delete "claim 15," and insert -- claim 13, --.

Signed and Sealed this

Twenty-ninth Day of September, 2009

David J. Kappos
*Director of the United States Patent and Trademark Office*